(12) United States Patent
Michaelis et al.

(10) Patent No.: US 7,078,399 B2
(45) Date of Patent: Jul. 18, 2006

(54) SULFHYDRYL RIFAMYCINS AND USES THEREOF

(75) Inventors: Arthur F. Michaelis, Devon, PA (US); Hawkins V. Maulding, Mendham, NJ (US); Chalom Sayada, Luxembourg (LU); Barry Eisenstein, Chestnut Hill, MA (US); William B. Geiss, Athens, NY (US); Joseph Raker, Delmar, NY (US)

(73) Assignee: ActivBiotics, Inc., Lexington, MA (US)

( * ) Notice: Subject to any disclaimer, the term of this patent is extended or adjusted under 35 U.S.C. 154(b) by 413 days.

(21) Appl. No.: 10/318,582

(22) Filed: Dec. 12, 2002

(65) Prior Publication Data

US 2004/0014749 A1 Jan. 22, 2004

Related U.S. Application Data

(60) Provisional application No. 60/412,958, filed on Sep. 23, 2002, provisional application No. 60/406,873, filed on Aug. 29, 2002, provisional application No. 60/385,532, filed on Jun. 3, 2002, provisional application No. 60/382,805, filed on May 23, 2002, provisional application No. 60/341,130, filed on Dec. 13, 2001.

(51) Int. Cl.
*C07D 405/02* (2006.01)
*A61K 31/496* (2006.01)
*A61P 31/04* (2006.01)

(52) U.S. Cl. .................................. 514/229.5; 540/456

(58) Field of Classification Search ................ 540/456; 514/229.5
See application file for complete search history.

(56) References Cited

U.S. PATENT DOCUMENTS

| | | | |
|---|---|---|---|
| 3,338,888 A | 8/1967 | Bickel et al. | |
| 4,086,225 A | 4/1978 | Marsili et al. | |
| 4,341,785 A | 7/1982 | Marchi et al. | |
| 4,557,866 A | 12/1985 | Cannata et al. | |
| 4,690,919 A | 9/1987 | Yamane et al. | |
| 4,859,661 A | 8/1989 | Kano et al. | |
| 4,965,261 A | 10/1990 | Kanoo et al. | |
| 4,983,602 A | 1/1991 | Yamane et al. | |
| 5,352,679 A | 10/1994 | Ferrieri et al. | |
| 5,547,683 A | 8/1996 | Yano et al. | |
| 5,786,349 A | 7/1998 | Yamashita et al. | |
| 5,981,522 A | 11/1999 | Yamashita et al. | |
| 6,486,161 B1 | 11/2002 | Fujii et al. | |

FOREIGN PATENT DOCUMENTS

JP 01-207293 8/1989

*Primary Examiner*—Bruck Kifle
(74) *Attorney, Agent, or Firm*—Clark & Elbing LLP

(57) ABSTRACT

The invention features sulfhydryl rifamycin compositions, methods of making these compositions, and methods for treating disease using these compositions.

15 Claims, 1 Drawing Sheet

SULFHYDRYL RIFAMYCINS AND USES THEREOF

CROSS-REFERENCE TO RELATED APPLICATIONS

The application claims benefit of U.S. Provisional Application Nos. 60/341,130, filed Dec. 13, 2001, 60/382,805, filed May 23, 2002, 60/385,532, filed Jun. 3, 2002, 60/406,873, filed Aug. 29, 2002, and 60/412,958, filed Sep. 23, 2002, which are hereby incorporated by reference.

BACKGROUND OF THE INVENTION

The present invention relates to the field of antimicrobial agents.

The use of antibiotics by humans can be seen as an evolutionary experiment of enormous magnitude, a window from which to view not-quite-natural selection operating in real time. Within 50 years, the number of species and strains of pathogenic and commensal bacteria resistant to antibiotics and the number of antibiotics to which they are resistant has increased virtually monotonically worldwide. As a result, infections that had been readily treatable by chemotherapy may no longer be so. It is clear that the evolution and spread of resistance can be attributed to the use and overuse of antibiotics. Increased resistance of bacterial infections to antibiotic treatment has been extensively documented and has now become a generally recognized medical problem, particularly with nosocomial infections. See, for example, Jones et al., Diagn. Microbiol. Infect. Dis. 31:379–388, 1998; Murray, Adv. Intern. Med. 42:339–367, 1997; and Nakae, Microbiologia 13:273–284, 1997.

Throughout the developed world there is public and governmental concern about the increasing prevalence of antimicrobial resistance to chemotherapy in bacteria that cause diseases in humans. Many pathogens exist for which there are few effective treatments, and the number of strains resistant to available drugs is continually increasing. New antimicrobial agents and improved methods are thus needed for the treatment and prevention of infections by such pathogens.

SUMMARY OF THE INVENTION

The present invention features sulfhydryl rifamycin compounds. These can be used as therapeutics for treating or preventing a variety of microbial infections.

In one aspect, the invention features a sulfhydryl rifamycin compound of formula I:

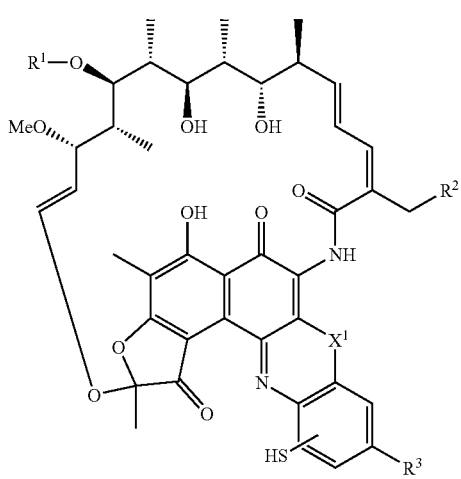

In formula I, $X^1$ represents an oxygen atom or a sulfur atom, $R^1$ represents a hydrogen or an acetyl group, $R^2$ represents a hydrogen or hydroxyl group, and $R^3$ represents a hydrogen atom or a group expressed by the formula:

wherein each of $R^4$ and $R^5$ is, independently, an alkyl group having 1 to 7 carbon atoms, or $R^4$ and $R^5$ combine to form a 3–8 membered cyclic system, or $R^3$ represents a group expressed by the formula:

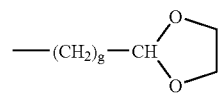

in which g represents an integer between 1 and 3;

or $R^3$ represents a group expressed by the formula:

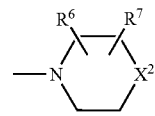

wherein each of $R^6$ and $R^7$ is, independently, a hydrogen atom or an alkyl group having 1 to 3 carbon atoms, $X^2$ represents an oxygen atom, a sulfur atom, or a carbonyl group, or $X^2$ represents a group expressed by the formula:

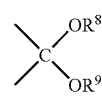

in which each of $R^8$ and $R^9$ is, independently, a hydrogen atom, or an alkyl group having 1 to 3 carbon atoms, or $R^8$ and $R^9$, in combination with each other, represent $—(CH_2)_k—$ in which k represents an integer between 1 and 4;

or $X^2$ represents a group expressed by the formula:

in which m represents 0 or 1, $R^{10}$ represents a hydrogen atom, an alkyl group having 1 to 6 carbon atoms, or $—(CH^2)_n X^3$ in which n represents an integer between 1 and 4, and $X^3$ represents an alkoxy group having 1 to 3 carbon atoms, a vinyl group, an ethynyl group, or $X^2$ represents a group expressed by the formula:

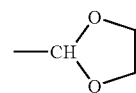

In further embodiments the sulfhydryl rifamycin compound is described by formula II:

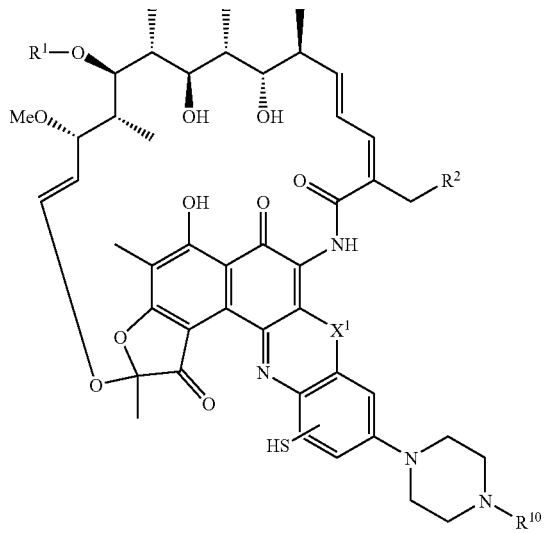

II wherein $R^1$ is hydrogen or an acetyl group, $R^2$ is hydrogen or a hydroxyl group, and $R^{10}$ is selected from the group consisting of methyl, ethyl, iso-propyl, n-propyl, iso-butyl, (S)-sec-butyl, and (R)-sec-butyl.

The invention also features methods of synthesizing sulfhydryl rifamycin compounds of formula I. A key intermediate in the synthesis is the preparation of a compound of formula VII:

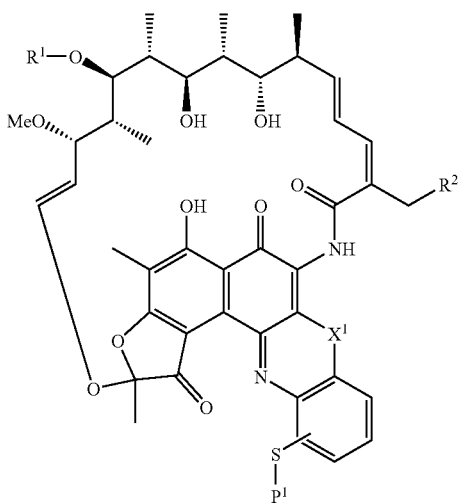

VII

The method includes reacting rifamycin S with a compound of formula VIII to produce a compound of formula VII.

VIII $$\begin{array}{c} Z^1 \\ H_2N \\ \diagdown \\ S \\ | \\ P^1 \end{array}$$

In formulas VII and VIII, $X^1$ represents an oxygen atom or a sulfur atom; $R^1$ represents a hydrogen or an acetyl group; $R^2$ represents a hydrogen or hydroxyl group; $Z^1$ represents a hydroxyl or sulfhydryl group; and $P^1$ represents a sulfhydryl protecting group. An exemplary sulfhydryl protecting group is betacyanoethyl. Desirably, the compound of formula VIII is further described by formula IX

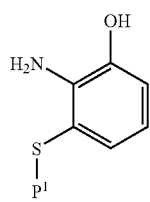

IX wherein $P^1$ is a sulfhydryl protecting group.

The invention also features a method for treating or preventing the development of an atherosclerosis-associated disease in a patient by administering to the patient a sulfhydryl rifamycin compound of formula I in an amount effective to treat or prevent the development of the atherosclerosis-associated disease in the patient. The patient is typically diagnosed as having the atherosclerosis-associated disease (or being at increased risk of developing the disease) or as having macrophages or foam cells infected with *C. pneumoniae* prior to the administration of the sulfhydryl rifamycin.

The invention also features a method of reducing the level of C-reactive protein in a patient in need thereof by administering to the patient a sulfhydryl rifamycin compound of formula I in an amount effective to reduce the level of C-reactive protein in the patient. In one embodiment, the patient has not been diagnosed as having a bacterial infection. In another embodiment, the patient has been diagnosed as having macrophages or foam cells infected with *C. pneumoniae*.

The invention also features a method for reducing *C. pneumoniae* replication in macrophages or foam cells in a patient in need thereof by administering a sulfhydryl rifamycin compound of formula I to the patient in an amount effective to reduce *C. pneumoniae* replication in macrophages or foam cells in the patient.

The invention also features a method for treating a persistent *C. pneumoniae* infection in macrophages or foam cells in a patient by administering a sulfhydryl rifamycin compound of formula I to the patient in an amount effective to treat the *C. pneumoniae* infection in macrophages or foam cells in the patient.

The invention also features a method for treating a chronic disease associated with an infection of *C. pneumoniae* by administering a sulfhydryl rifamycin compound of formula I to the patient in an amount effective to treat the infection.

In any of the foregoing aspects, the dosage of the sulfhydryl rifamycin compound is normally about 0.001 to 100 mg/day. The compound may be given daily (e.g., a single oral dose of 2.5 to 25 mg/day) or less frequently (e.g., a single oral dose of 5, 12.5, or 25 mg/week). Treatment may be for one day to one year, or longer. In one embodiment, a sulfhydryl rifamycin compound is administered at an initial does of 2.5 to 100 mg for one to seven consecutive days, followed by a maintenance dose of 0.005 to 10 mg once every one to seven days for one month, one year, or even for the life of the patient.

If desired, a sulfhydryl rifamycin compound may be administered in conjunction with one or more additional agents such as anti-inflammatory agents (e.g., non-steroidal anti-inflammatory drugs (NSAIDs; e.g., detoprofen, diclofenac, diflunisal, etodolac, fenoprofen, flurbiprofen, ibuprofen, indomethacin, ketoprofen, meclofenameate, mefenamic acid, meloxicam, nabumeone, naproxen sodium, oxaprozin, piroxicam, sulindac, tolmetin, celecoxib, rofecoxib, aspirin, choline salicylate, salsalte, and sodium and magnesium salicylate) and steroids (e.g., cortisone, dexamethasone, hydrocortisone, methylprednisolone, prednisolone, prednisone, triamcinolone)), antibacterial agents (e.g., azithromycin, clarithromycin, erythromycin, gatifloxacin, levofloxacin, amoxicillin, or metronidazole), platelet aggregation inhibitors (e.g., abciximab, aspirin, cilostazol, clopidogrel, dipyridamole, eptifibatide, ticlopidine, or tirofiban), anticoagulants (e.g., dalteparin, danaparoid, enoxaparin, heparin, tinzaparin, or warfarin), antipyretics (e.g., acetaminophen), or lipid lowering agents (e.g., cholestyramine, colestipol, nicotinic acid, gemfibrozil, probucol, ezetimibe, or statins such as atorvastatin, rosuvastatin, lovastatin simvastatin, pravastatin, cerivastatin, and fluvastatin). These additional agents may be administered within 14 days, 7 days, 1 day, 12 hours, or 1 hour of administration of the sulfhydryl rifamycin compound, or simultaneously therewith. The additional therapeutic agents may be present in the same or different pharmaceutical compositions as the sulfhydryl rifamycin compound. When present in different pharmaceutical compositions, different routes of administration may be used. For example, the sulfhydryl rifamycin compound may be administered orally, while a second agent may be administered by intravenous, intramuscular, or subcutaneous injection.

The invention also features a stent coated with a sulfhydryl rifamycin compound of formula I. The stent can be, e.g., a wire mesh tube used to hold open an artery. Stents are typically inserted following angioplasty.

The invention also features methods and compositions for treating or preventing an ear infection in a patient by topically administering to the affected otic area (e.g., the tympanic membrane or the external auditory canal of the ear) of the patient a pharmaceutical composition including a therapeutically effective amount of a sulfhydryl rifamycin compound of formula I. The compositions and methods of the invention can also be used to treat or prevent infections that result from surgery.

The invention also features a pharmaceutical composition suitable for topical administration to the ear of a patient containing a sulfhydryl rifamycin compound of formula I and a pharmaceutically-acceptable excipient, administered at a dose capable of reducing the infection in the patient. According to this invention, the sulfhydryl rifamycin compound of formula I can be in the amount between 0.001% and 5% weight/volume (w/v), preferably 0.01% and 3% w/v, more preferably 0.1% and 1% w/v, or most preferably 0.1% and 0.4% w/v. The rifamycin may also be impregnated in a porous media (for example, an ear wick such as a sponge, gauze, cotton, or hydrocellulose), which is suitable for insertion into the ear of a patient. If desired, the composition may also include one or more penetration enhancers (e.g., alcohols, polyols, sulfoxides, esters, ketones, amides, oleates, surfactants, alkanoic acids, lactam compounds, alkanols, or admixtures thereof).

In another aspect, the invention also features a method for treating or preventing the development of an ear infection in a patient using a composition described above. The sulfhydryl rifamycin compound of formula I can be administered to the infected ear by means of drops or by the insertion of a rifamycin-impregnated porous media into the external ear canal to the tympanic membrane. Ear infections that can be treated using the methods and composition of the invention include otitis media and otitis externa. Types of otitis media amenable to treatment include, for example, acute otitis media, otitis media with effusion, and chronic otitis media. Types of otitis externa include acute otitis externa, chronic otitis externa, and malignant otitis externa. A rifamycin of the invention is administered to the ear (e.g., the tympanic membrane or the external auditory canal of the ear) to treat or prevent bacterial infections associated with otitis media (e.g., an infection of *H. influenza, M. catarhalis,* or *S. pneumoniae*) or in otitis externa (e.g., an infection of *S. intermedius, Streptococcus* spp. *Pseudomonas* spp., *Proteus* spp., or *E. coli*).

The methods and compositions of the invention are also useful to treat infections associated with otic surgical procedures such as tympanoplasty, stapedectomy, removal of tumors, or cochlear implant surgery. The compositions may also be used prophylactically, prior to therapies or conditions that can cause ear infections. Compositions containing a sulfhydryl rifamycin compound of formula I can therefore be applied to an area of the ear to which the surgical intervention will be performed, within at least seven days (before or after) of the surgical intervention. When treating a patient affected with otitis externa, an acidification therapy involving the administration of an acetic acid solution to the ear of the patient may also be performed.

Typically, patients are administered one to four drops of a sulfhydryl rifamycin compound of the invention in a total amount between 0.001% and 5% w/v, preferably 0.01% and 3% w/v, more preferably 0.1% and 1% w/v, or most preferably 0.1% and 0.4% w/v. The composition may be given daily (e.g., once, twice, three times, or four times daily) or less frequently (e.g., once every other day, or once or twice weekly). Treatment may be for 1 to 21 days, desirably 1 to 14 days, or even 3 to 7 days. Additional therapeutic agents, such as anti-inflammatory agents (e.g., non-steroidal anti-inflammatory or steroid), anesthetics, zinc salts, or other antimicrobial agents, can also be administered with the rifamycin of the invention. Non-steroidal anti-inflammatory agents include, for example, detoprofen, diclofenac, diflunisal, etodolac, fenoprofen, flurbiprofen, indomethacin, ketoprofen, mechlofenameate, mefenamic acid, meloxicam, nabumeone, naproxen sodium, oxaprozin, piroxicam, sulindac, tolmeting, celecoxib, rofecoxib, choline salicylate, salsate, sodium salicylate, magnesium salicylate, aspirin, ibuprofen, paracetamol, acetaminophen, and pseudoephedrine and steroids include, for example, hydrocortisone, prednisone, fluprednisolone, triamcinolone, dexamethasone, betamethasone, cortisone, prednilosone, methylprednisolone, fluocinolone acetonide, flurandrenolone acetonide, and fluorometholone. Anesthetics according to the invention can be, for example, benzocaine, butamben picrate, tetracaine, dibucaine, prilocaine, etidocaine, mepivacaine, bupivicaine, and lidocaine. A zinc salt can be zinc sulfate, zinc chloride, zinc acetate, zinc phenol sulfonate, zinc borate, zinc bromide, zinc nitrate, zinc glycerophosphate, zinc benzoate, zinc carbonate, zinc citrate, zinc hexafluorosilicate, zinc diacetate trihydrate, zinc oxide, zinc peroxide, zinc salicylate, zinc silicate, zinc stannate, zinc tannate, zinc titanate, zinc tetrafluoroborate, zinc gluconate, and zinc glycinate, and antimicrobial agents according to the invention include, for example, amoxillin, erythromycin, azithromycin, clarithromycin, gentamicin, tobramycin, ciprofloxaxin, norfloxacin, gatifloxacin, ofloxacin, levofloxacin, moxifloxacin, metronidazole, lomefloxacin, ciprofloxacin, natamycin, neomycin, polymyxin B, gentamycin, trovafloxacin, grepafloxacin, sulfacetamide, tetracycline, gramicidin, chloremphenicol, bacitracin, and gramicidin. These additional therapeutic agents can be present in the same or different pharmaceutical compositions as the sulfhydryl rifamycin compound of formula I. When a therapeutic agent is present in a different pharmaceutical composition, different routes of administration may be used. The sulfhydryl rifamycin compound of formula I and the second therapeutic agent, for example, may also be administered within 24 hours of each other, and an anti-inflammatory agent, for example, may be administered orally, or by intravenous, intramuscular, or subcutaneous injection.

To increase the efficacy of the topically administered rifamycin-containing composition, it is desirable that the amount of debris and granulation tissue are reduced in the infected ear of the patient at least one hour prior to the administration of the rifamycin and at least once a day. Debris can be removed, for example, by suction, irrigation with a solution containing hydrogen peroxide, cauterization, or by manual techniques employing microinstruments and microscope. Reduction in the amount of granulation tissue in the infected ear may be performed by means of cautering, or by the administration of a steroid.

The invention also features a pharmaceutical pack containing (i) a sulfhydryl rifamycin compound of formula I in an amount effective to treat a patient having an ear infection; and (ii) instructions for administering the compound to the ear of a patient. The invention also features a container containing a sulfhydryl rifamycin compound of formula I and a pharmaceutical excipient suitable for topical administration to the ear. If desired, an applicator for applying the composition to the ear may also be included. Desirably, the sulfhydryl rifamycin compound can be in the amount between 0.001% and 5% weight/volume (w/v), preferably 0.01% and 3% w/v, more preferably 0.1% and 1% w/v, or most preferably 0.1% and 0.4% w/v and is present in amounts sufficient to treat for at least 1, 3, 5, 7, 10, 14, or 21 days. A penetration enhancer may also be added (e.g., alcohols, polyols, sulfoxides, esters, ketones, amides, oleates, surfactants, alkanoic acids, lactam compounds, alkanols, or admixtures thereof).

The invention also features a method for treating chronic gastritis, gastric ulcer, or duodenal ulcer associated with an infection of *H. pylori*, or preventing the disease or infection, in a patient. The method includes the step of orally administering to the patient an effective amount of a sulfhydryl rifamycin compound of formula I to treat the patient. The compound is normally about 1 to 1000 mg/day (desirably about 1 to 100 mg/day, more desirably about 5 to 50 mg/day, and even more desirably about 5 to 25 mg/day). The compound may be given daily (e.g., once, twice, three times, or four times daily) or less frequently (e.g., once every other day, or once or twice weekly). Treatment may be for 1 to 21 days, desirably 1 to 14 days or even 3 to 7 days. If desirable, a sulfhydryl rifamycin compound can be administered with a proton pump inhibitor (e.g., omeprazole, esomeprazole, lansoprazole, leminoprazole, pantoprazole or robeprazole), and/or bismuth preparation (e.g., colloidal bismuth subcitrate or bismuth subsalicylate).

The invention also features a pharmaceutical pack including (i) a sulfhydryl rifamycin compound of formula I in an amount effective to treat chronic gastritis, gastric ulcer, or duodenal ulcer associated with an infection of *H. pylori* in a patient; and (ii) instructions for administering the compound to the patient. Desirably, the compound is in unit amounts of between 1 and 1000 mg (e.g, between 1 and 50 mg or between 5 and 5 mg), and is present in amounts sufficient to treat for at least 1, 3 5, 7, 10, 14, or 21 days. The pack may optionally include a proton pump inhibitor and/or bismuth preparation. In one embodiment, the sulfhydryl rifamycin compound of formula I is in a pharmaceutical composition with the proton pump inhibitor and/or bismuth preparation.

The invention also features a method for treating a patient having antibiotic-associated bacterial diarrhea or an infection of *C. difficile*, or preventing the disease or infection in the patient. The method includes the step of orally administering to the patient an effective amount of a sulfhydryl rifamycin compound of formula I to treat the patient. The compound is normally about 1 to 1000 mg/day (desirably about 1 to 100 mg/day, more desirably about 5 to 50 mg/day, and even more desirably about 5 to 25 mg/day). The compound may be given daily (e.g., once, twice, three times, or four times daily) or less frequently (e.g., once every other day, or once or twice weekly). Treatment may be for 1 to 21 days, desirably 1 to 14 days or even 3 to 7 days. In one embodiment, a sulfhydryl rifamycin compound is administered at an initial dose of between 5 and 100 mg, followed by subsequent doses of between 1 and 50 mg for 3 to 7 days. A single dose (e.g., in a dosage of between 5 and 50 mg) can also be employed in the method of the invention. If desirable, a sulfhydryl rifamycin compound can be administered with a second antibiotic (e.g., metronidazole).

The invention also features a pharmaceutical pack including (i) a sulfhydryl rifamycin compound of formula I in an amount effective to treat a patient having antibiotic-associated bacterial diarrhea or an infection of *C. difficile*; and (ii) instructions for administering the compound to the patient for treating or preventing a *C. difficile* infection. Desirably, the compound is in unit amounts of between 1 and 1000 mg (e.g, between 1 and 50 mg or between 5 and 5 mg), and is present in amounts sufficient to treat for at least 1, 3 5, 7, 10, 14, or 21 days.

The invention features a method for treating a patient having an infection of *Chlamydia trachomatis*. The method includes the step of administering to the patient a single oral dose of a sulfhydryl rifamycin compound of formula I in an amount effective to treat the patient.

The invention also features a pharmaceutical pack that includes (i) a single oral dose of a sulfhydryl rifamycin compound of formula I in an amount effective to treat a patient having an infection of *C. trachomatis* or *N. gonorrhoeae*; and (ii) instructions for administering the single oral dose to the patient. Desirably, the dose is in an amount between 0.1 and 100 mg (e.g., between 1 and 50 mg or between 5 and 25 mg).

The invention also features a method of treating a patient having a chronic disease associated with a bacterial infection caused by bacteria capable of establishing a cryptic phase. This method includes the step of administering to a patient a sulfhydryl rifamycin compound of formula I for a time and in an amount sufficient to treat the cryptic phase of the bacterial infection. The chronic disease may be an inflammatory disease. Examples of inflammatory diseases include but are not limited to asthma, coronary artery disease, arthritis, conjunctivitis, lymphogranuloma venerum (LGV), cervicitis, and salpingitis. The chronic disease can also be an autoimmune disease (e.g., systemic lupus erythematosus, diabetes mellitus, graft versus host disease).

The invention further features a method of treating the non-replicating, cryptic phase of a bacterial infection. This method includes the step of administering to a patient a sulfhydryl rifamycin formula I for a time and in an amount sufficient to treat the cryptic phase of the bacterial infection.

The invention also features a method of treating a bacterial infection in a patient by (a) treating the replicating phase or the elementary body phase of the chlamydial life cycle by administering an anti-bacterial agent to the patient for a time and an amount sufficient to treat the replicating phase or elementary body phase, and (b) treating the cryptic phase of the infection by administering to the patient a sulfhydryl rifamycin compound of formula I, wherein the administering is for a time and in an amount sufficient to treat the cryptic phase of the infection.

In a related aspect, the invention features a method of treating a chronic disease associated with a persistent intracellular bacterial infection or treating the persistent bacterial infection itself by administering a sulfhydryl rifamycin compound of formula I. As used herein, monotherapy is defined as a therapy in which the sulfhydryl rifamycin compound is the only antibacterial agent present in amounts sufficient to treat the cryptic phase of the infection.

In preferred embodiments of any of the foregoing aspects, the persistent intracellular bacterial infection is caused by one of the following: *Chlamydia* spp. (e.g., *C. trachomatis, C. pneumoniae, C. psittaci, C. suis, C. pecorum, C. abortus, C. caviae, C. felis, C. muridarum*), *N. hartmannellae, W. chondrophila, S. negevensis,* or *P. acanthamoeba.*

The time sufficient to treat the cryptic phase of the bacterial infection ranges from one week to one year, but it can also be extended over the lifetime of the individual patient, if necessary. In more preferable embodiments, the duration of treatment is at least 30 days, at least 45 days, at least 90 days, or at least 180 days. Ultimately, it is most desirable to extend the treatment for such a time that the intracellular bacterial infection is no longer detected.

In another aspect, the invention features a method of preventing, stabilizing, or inhibiting the growth of microbes, or killing microbes. The method includes contacting microbes or a site susceptible to microbial growth with one or more compounds of the invention in amounts sufficient to prevent, stabilize, or inhibit the growth of the microbes, or kill the microbes.

The sulfhydryl rifamycin compounds of formula I are useful against drug resistant Gram-positive cocci such as methicillin-resistant *S. aureus* and vancomycin-resistant enterococci, and are useful in the treatment of community-acquired pneumonia, upper and lower respiratory tract infections, skin and soft tissue infections, hospital-acquired lung infections, bone and joint infections, and other bacterial infections.

In one embodiment of the above aspect, the step of contacting microbes or a site susceptible to microbial growth with the compound includes administering to an animal the compound in an amount sufficient to treat, stabilize, or prevent the microbial infection.

The microbial infection to be treated or prevented by the compound of the invention can be an infection by a bacterium, such as *Acinetobacter calcoaceticus, A. haemolyticus, Aeromonas hydrophilia, Bacteroides fragilis, B. distasonis,* Bacteroides 3452A homology group, *B. vulgatus, B. ovalus, B. thetaiotaomicron, B. uniformis, B. eggerthii, B. splanchnicus, Branhamella catarrhalis, Campylobacter fetus, C. jejuni, C. coli, Citrobacter freundii, Clostridium difficile, C. diphtheriae, C. ulcerans, C. accolens, C. afermentans, C. amycolatum, C. argentorense, C. auris, C. bovis, C. confusum, C. coyleae, C. durum, C. falsenii, C. glucuronolyticum, C. imitans, C. jeikeium, C. kutscheri, C. kroppenstedtii, C. lipophilum, C. macginleyi, C. matruchoti, C. mucifaciens, C. pilosum, C. propinquum, C. renale, C. riegelii, C. sanguinis, C. singulare, C. striatum, C. sundsvallense, C. thomssenii, C. urealyticum, C. xerosis, Enterobacter cloacae, E. aerogenes, Enterococcus avium, E. casseliflavus, E. cecorum, E. dispar, E. durans, E. faecalis, E. faecium, E. flavescens, E. gallinarum, E. hirae, E. malodoratus, E. mundtii, E. pseudoavium, E. raffinosus, E. solitarius, Francisella tularensis, Gardnerella vaginalis, Helicobacter pylori, Kingella dentrificans, K. kingae, K. oralis, Klebsiella pneumoniae, K oxytoca, Moraxella catarrhalis, M. atlantae, M. lacunata, M. nonliquefaciens, M. osloensis, M. phenylpyruvica, Morganella morganii, Parachlamydia acanthamoebae, Pasteurella multocida, P. haemolytica, Proteus mirabilis, Proteus vulgaris, Providencia alcalifaciens, P. rettgeri, P. stuartii, Serratia marcescens, Simkania negevensis, Streptococcus pneumoniae, S. agalactiae, S. pyogenes, Treponema pallidum, Vibrio cholerae,* and *V. parahaemolyticus.* Accordingly, the invention features a method of treating infections by the bacteria above, among others.

In another embodiment, the microbial infection to be treated or prevented by one or more compounds of the invention is an intracellular infection by a facultative or obligate intracellular microbe.

Compounds of the invention may be used to treat or prevent bacterial infections by facultative intracellular bacteria, such as *Bordetella pertussis, B. parapertussis, B. bronchiseptica, Burkholderia cepacia, Escherichia coli, Haemophilus actinomycetemcomitans, H. aegyptius, H. aphrophilus, H. ducreyi, H. felis, H. haemoglobinophilus, H. haemolyticus, H. influenzae, H. paragallinarum, H. parahaemolyticus, H. parainfluenzae, H. paraphrohaemolyticus, H. paraphrophilus, H. parasuis, H. piscium, H. segnis, H. somnus, H. vaginalis, Legionella adelaidensis, L. anisa, L. beliardensis, L. birminghamensis, L. bozemanii, L. brunensis, L. cherrii, L. cincinnatiensis, Legionella drozanskii L. dumoffli, L. erythra, L. fairfieldensis, L. fallonii, L. feeleii, L. geestiana, L. gormanii, L. gratiana, L. gresilensis, L. hackeliae, L. israelensis, L. jordanis, L. lansingensis, Legionella londiniensis L. longbeachae, Legionella lytica L. maceachernii, L. micdadei, L. moravica, L. nautarum, L. oakridgensis, L. parisiensis, L. pittsburghensis, L. pneumophila, L. quateirensis, L. quinlivanii, L. rowbothamii, L. rubrilucens, L. sainthelensi, L. santicrucis, L. shakespearei, L. spiritensis, L. steigerwaltii, L. taurinensis, L. tucsonensis, L. wadsworthii, L. waltersii, L. worsleiensis, Listeria denitrificans, L. grayi, L. innocua, L. ivanovii, L. monocytogenes, L. seeligeri, L. welshimeri, Mycobacterium abscessus, M. africanum, M. agri, M. aichiense, M. alvei, M. asiaticum, M. aurum, M. austroafricanum, M. avium, M. bohemicum, M. bovis, M. branderi, M. brumae, M. celatum, M. chelonae, M. chitae, M. chlorophenolicum, M. chubuense, M. confluentis, M. conspicuum, M. cookii, M. diernhoferi, M. doricum, M. duvalii, M. elephantis, M. fallax, M. farcinogenes, M. flavescens, M. fortuitum, M. frederiksbergense, M. gadium, M. gastri, M. genavense, M. gilvum, M. goodii, M. gordonae, M. haemophilum, M. hassiacum, M. heckeshornense, M. heidelbergense, M. hiberniae, M. immunogenum, M. intracellulare, M. interjectum, M. intermedium, M. kansasii, M. komossense, M. kubicae, M. lentiflavum, M. leprae, M. lepraemurium, M. luteum, M. madagascariense, M. mageritense, M. malmoense, M. marinum, M. microti, M. moriokaense, M. mucogenicum, M. murale, M. neoaurum, M.* nonchromogenicum, M. novocastrense, M. obuense, M. parafortuitum, M. paratuberculosis, M. peregrinum, M. phage, M. phlei, M. porcinum, M. poriferae, M. pulveris, M. rhodesiae, M. scrofulaceum, M. senegalense, M. septicum, M. shimoidei, M. simiae, M. smegmatis, M. sphagni, M. szulgai, M. terrae, M. thermoresistibile, M. tokaiense, M. triplex, M. triviale, M. tuberculosis, M. tusciae, M. ulcerans, M. vaccae, M. wolinskyi, M. xenopi, Neisseria animalis, N. canis, N. cinerea, N. denitrificans, N. dentiae, N. elongata, N. flava, N. flavescens, N. gonorrhoeae, N. iguanae, N. lactamica, N. macacae, N. meningitidis, N. mucosa, N. ovis, N. perflava, N. pharyngis var. flava, N. polysaccharea, N. sicca, N. subflava, N. weaveri, Pseudomonas aeruginosa, P. alcaligenes, P. chlororaphis, P. fluorescens, P. luteola, P. mendocina, P. monteilii, P. oryzihabitans, P. pertocinogena, P. pseudalcaligenes, P. putida, P. stutzeri, Salmonella bacteriophage, S. bongori, S. choleraesuis, S. enterica, S. enteritidis, S. paratyphi, S. typhi, S. typhimurium, S. typhimurium, S. typhimurium, S. typhimurium bacteriophage, Shigella boydii, S. dysenteriae, S. flexneri, S. sonnei, Staphylococcus arlettae, S. aureus, S. auricularis, S. bacteriophage, S. capitis, S. caprae, S. carnosus, S. caseolyticus, S. chromogenes, S. cohnii, S. delphini, S. epidermidis, S. equorum, S. felis, S. fleurettii, S. gallinarum, S. haemolyticus, S. hominis, S. hyicus, S. intermedius, S. kloosii, S. lentus, S. lugdunensis, S. lutrae, S. muscae, S. mutans, S. pasteuri, S. phage, S. piscifermentans, S. pulvereri, S. saccharolyticus, S. saprophyticus, S. schleiferi, S. sciuri, S. simulans, S. succinus, S. vitulinus, S. warneri, S. xylosus, Ureaplasma urealyticum, Yersinia aldovae, Y. bercovieri, Y. enterocolitica, Y. frederiksenii, Y. intermedia, Y. kristensenii, Y. mollaretii, Y. pestis, Y. philomiragia, Y. pseudotuberculosis, Y. rohdei, and Y. ruckeri. Compounds of the invention may also be used to treat or prevent bacterial infections by obligate intracellular bacteria, such as Anaplasma bovis, A. caudatum, A. centrale, A. marginale A. ovis, A. phagocytophila, A. platys, Bartonella bacilliformis, B. clarridgeiae, B. elizabethae, B. henselae, B. henselae phage, B. quintana, B. taylorii, B. vinsonii, Borrelia afzelii, B. andersonii, B. anserina, B. bissettii, B. burgdorferi, B. crocidurae, B. garinii, B. hermsii, B. japonica, B. miyamotoi, B. parkeri, B. recurrentis, B. turdi, B. turicatae, B. valaisiana, Brucella abortus, B. melitensis, Chlamydia pneumoniae, C. psittaci, C. trachomatis, Cowdria ruminantium, Coxiella burnetii, Ehrlichia canis, E. chaffeensis, E. equi, E. ewingii, E. muris, E. phagocytophila, E. platys, E. risticii, E. ruminantium, E. sennetsu, Haemobartonella canis, H. felis, H. muris, Mycoplasma arthriditis, M. buccale, M. faucium, M. fermentans, M. genitalium, M. hominis, M. laidlawii, M. lipophilum, M. orale, M. penetrans, M. pirum, M. pneumoniae, M. salivarium, M. spermatophilum, Rickettsia australis, R. conorii, R. felis, R. helvetica, R. japonica, R. massiliae, R. montanensis, R. peacockii, R. prowazekii, R. rhipicephali, R. rickettsii, R. sibirica, and R. typhi. Accordingly, the invention features a method of treating infections caused by the obligate and facultative intracellular bacteria above, among others.

Compounds of the invention may be used to treat or prevent fungal infections by a facultative intracellular fungi, such as Candida aaseri, C. acidothermophilum, C. acutus, C. albicans, C. anatomiae, C. apis, C. apis var. galacta, C. atlantica, C. atmospherica, C. auringiensis, C. bertae, C. berthtae var. chiloensis, C. berthetii, C. blankii, C. boidinii, C. boleticola, C. bombi, C. bombicola, C. buinensis, C. butyri, C. cacaoi, C. cantarellii, C. cariosilignicola, C. castellii, C. castrensis, C. catenulata, C. chilensis, C. chiropterorum, C. coipomensis, C. dendronema, C. deserticola, C. diddensiae, C. diversa, C. entomaea, C. entomophila, C. ergatensis, C. ernobii, C. ethanolica, C. ethanothermophilum, C. famata, C. fluviotilis, C. fragariorum, C. fragicola, C. friedrichii, C. fructus, C. geochares, C. glabrata, C. glaebosa, C. gropengiesseri, C. guilliermondii, C. guilliermondii var. galactosa, C. guilliermondii var. soya, C. haemulonii, C. halophila/C. versatilis, C. holmii, C. humilis, C. hydrocarbofumarica, C. inconspicua, C. insectalens, C. insectamans, C. intermedia, C. javanica, C. kefyr, C. krissii, C. krusei, C. krusoides, C. lambica, C. lusitaniae, C. magnoliae, C. maltosa, C. mamillae, C. maris, C. maritima, C. melibiosica, C. melinii, C. methylica, C. milleri, C. mogii, C. molischiana, C. montana, C. multis-gemmis, C. musae, C. naeodendra, C. nemodendra, C. nitratophila, C. norvegensis, C. norvegica, C. oleophila, C. oregonensis, C. osornensis, C. paludigena, C. parapsilosis, C. pararugosa, C. periphelosum, C. petrohuensis, C. petrophilum, C. philyla, C. pignaliae, C. pintolopesii var. pintolopesii, C. pintolopesii var. slooffiae, C. pinus, C. polymorpha, C. populi, C. pseudointermedia, C. quercitrasa, C. railenensis, C. rhagii, C. rugopelliculosa, C. rugosa, C. sake, C. salmanticensis, C. savonica, C. sequanensis, C. shehatae, C. silvae, C. silvicultrix, C. solani, C. sonorensis, C. sorbophila, C. spandovensis, C. sphaerica, C. stellata, C. succiphila, C. tenuis, C. terebra, C. tropicalis, C. utilis, C. valida, C. vanderwaltii, C. vartiovaarai, C. veronae, C. vini, C. wickerhamii, C. xestobii, C. zeylanoides, and Histoplasma capsulatum. Accordingly, the invention features a method of treating an infection by the facultative intracellular fungi above, among others.

Obligate intracellular protozoans can also be treated by a compound of the invention. Obligate intracellular protozoans include, for example, Brachiola vesicularum, B. connori, Encephalitozoon cuniculi, E. hellem, E. intestinalis, Enterocytozoon bieneusi, Leishmania aethiopica, L. amazonensis, L. braziliensis, L. chagasi, L. donovani, L. donovani chagasi, L. donovani donovani, L. donovani infantum, L. enriettii, L. guyanensis, L. infantum, L. major, L. mexicana, L. panamensis, L. peruviana, L. pifanoi, L. tarentolae, L. tropica, Microsporidium ceylonensis, M. africanum, Nosema connori, N. ocularum, N. algerae, Plasmodium berghei, P. brasilianum, P. chabaudi, P. chabaudi adami, P. chabaudi chabaudi, P. cynomolgi, P. falciparum, P. fragile, P. gallinaceum, P. knowlesi, P. lophurae, P. malariae, P. ovale, P. reichenowi, P. simiovale, P. simium, P. vinckei petteri, P. vinckei vinckei, P. vivax, P. yoelii, P. yoelii nigeriensis, P. yoelii yoelii, Pleistophora anguillarum, P. hippoglossoideos, P. mirandellae, P. ovariae, P. typicalis, Septata intestinalis, Toxoplasma gondii, Trachipleistophora hominis, T. anthropophthera, Vittaforma corneae, Trypanosoma avium, T. brucei, T. brucei brucei, T. brucei gambiense, T. brucei rhodesiense, T. cobitis, T. congolense, T. cruzi, T. cyclops, T. equiperdum, T. evansi, T. dionisii, T. godfreyi, T. grayi, T. lewisi, T. mega, T. microti, T. pestanai, T. rangeli, T. rotatorium, T. simiae, T. theileri, T. varani, T. vespertilionis, and T. vivax. Accordingly, the invention features a method of treating infections by the obligate intracellular protozoa above, among others.

Compounds of the invention may also be used to treat or prevent viral infections.

In another aspect, the invention features a pharmaceutical composition that includes a compound described herein in any pharmaceutically acceptable form, including isomers such as diastereomers and enantiomers, salts, solvates, and polymorphs thereof. In various embodiments, the composition includes a compound of the invention along with a pharmaceutically acceptable carrier or diluent.

In another aspect, the invention features a method of treating a microbial infection in an animal comprising co-administering a compound of the invention along with one or more antifungal agents, antiviral agents, antibacterial agents, or antiprotozoan agents, or combinations thereof.

In any of the above aspects, desirable sulfhydryl rifamycin compounds of formula I include compounds 7–9, shown below.

compound 7

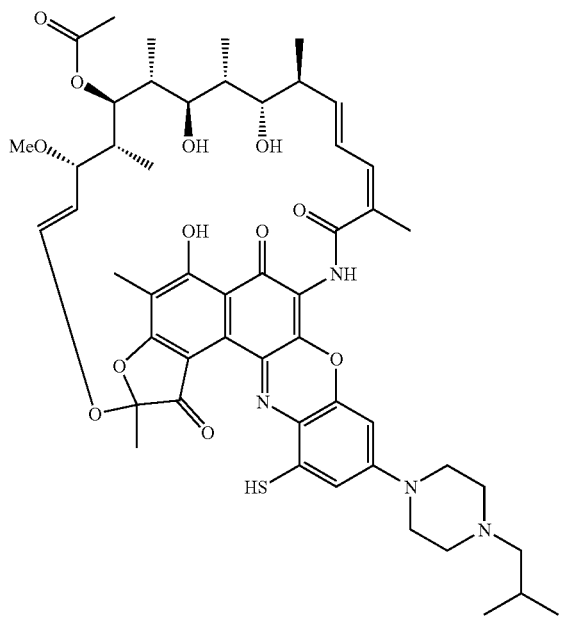

compound 8

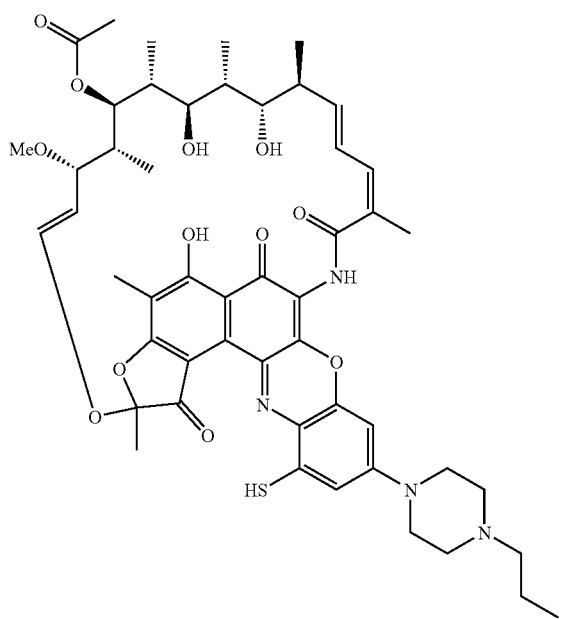

compound 9

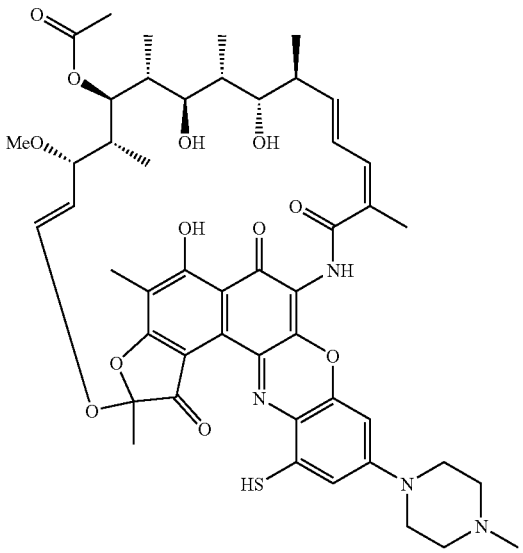

In the generic descriptions of compounds of this invention, the number of atoms of a particular type in a substituent group is generally given as a range, for example, as an alkyl group containing from 1 to 10 carbon atoms. Reference to such a range is intended to include specific references to groups having each of the integer number of atoms within the specified range. For example, an alkyl group from 1 to 10 carbon atoms includes each of $C_1$, $C_2$, $C_3$, $C_4$, $C_5$, $C_6$, $C_7$, $C_8$, $C_9$, and $C_{10}$. Other numbers of atoms and other types of atoms are indicated in a similar manner.

By "alkyl" is meant a branched or unbranched saturated hydrocarbon group, desirably having from 1 to 10 or 1 to 15 carbon atoms. An alkyl may optionally include monocyclic, bicyclic, or tricyclic rings, in which each ring desirably has three to six members. The alkyl group may be substituted or unsubstituted. Exemplary substituents include alkoxy, aryloxy, sulfhydryl, alkylthio, arylthio, halogen, hydroxyl, fluoroalkyl, perfluoroalkyl, amino, aminoalkyl, disubstituted amino, quaternary amino, hydroxyalkyl, carboxyalkyl, and carboxyl groups.

The term "cyclic system" refers to a compound that contains one or more covalently closed ring structures, in which the atoms forming the backbone of the ring are composed of any combination of the following carbon, oxygen, nitrogen, sulfur, and phosphorous. The cyclic system may be substituted or unsubstituted. Exemplary substituents include alkyl, hydroxyl, alkoxy, aryloxy, sulfhydryl, alkylthio, arylthio, halogen, fluoroalkyl, carboxyl, carboxyalkyl, amino, aminoalkyl, monosubstituted amino, disubstituted amino, and quaternary amino groups.

By "fluoroalkyl" is meant an alkyl group that is substituted with a fluorine.

By "perfluoroalkyl" is meant an alkyl group consisting of only carbon and fluorine atoms.

By "carboxyalkyl" is meant a chemical moiety with the formula —(R)—COOH, wherein R is an alkyl group.

By "hydroxyalkyl" is meant a chemical moiety with the formula —(R)—OH, wherein R is an alkyl group.

By "alkoxy" is meant a chemical substituent of the formula —OR, wherein R is an alkyl group.

By "aryloxy" is meant a chemical substituent of the formula —OR, wherein R is an aryl group.

By "alkylthio" is meant a chemical substituent of the formula —SR, wherein R is an alkyl group.

By "arylthio" is meant a chemical substituent of the formula —SR, wherein R is an aryl group.

By "quaternary amino" is meant a chemical substituent of the formula —(R)—N(R')(R'')(R''')$^+$, wherein R, R', R'', and R''' are each independently an alkyl, alkene, alkyne, or aryl group. R may be an alkyl group linking the quaternary amino nitrogen atom, as a substituent, to another moiety. The nitrogen atom, N, is covalently attached to four carbon atoms of alkyl and/or aryl groups, resulting in a positive charge at the nitrogen atom.

By "sulfhydryl protecting group" is meant a labile moiety which forms a covalent bond with a sulfhydryl and which can be removed, or an oxidized or reduced form of a sulfhydryl from which a sulfhydryl formed (e.g., by oxidation of a reduced form or reduction of an oxidized form). Labile sulfhydryl protecting groups include thioethers and thioesters. Examples of thioethers include methyl, betacyanoethyl, methoxymethyl, methoxyethoxymethyl, methylthiomethyl, benzyloxymethyl, tetrahydropyranyl, ethoxyethyl, benzyl, 2-napthylmethyl, O-nitrobenzyl, P-nitrobenzyl, P-methoxybenzyl, 9-phenylxanthyl, trityl (including methoxy-trityls), and silyl thioethers. Sulfhydryls can be protected in a reduced form (e.g., as disulfides) or an oxidized form (e.g., as sulfonic acids, sulfonic esters, or sulfonic amides). Sulfhydryl protecting groups that can be used in accordance with the present invention include those described in T. W. Green and P. G. M. Wuts, "Protective Groups in Organic Synthesis" ($2^{nd}$ Ed.), John Wiley & Sons, 1991 and P. J. Kocienski, "Protecting Groups," Georg Thieme Verlag, 1994, each of which is hereby incorporated by reference.

By "atherosclerosis" is meant the progressive accumulation of smooth muscle cells, immune cells (e.g., lymphocytes, macrophages, or monocytes), lipid products (e.g., lipoproteins, or cholesterol), cellular waste products, calcium, or other substances within the inner lining of an artery, resulting in the narrowing or obstruction of the blood vessel and the development of atherosclerosis-associated diseases. Atherosclerosis is typically manifested within large and medium-sized arteries, and is often characterized by a state of chronic inflammation within the arteries.

By "atherosclerosis-associated disease" is meant any disorder that is caused by or is associated with atherosclerosis. Typically, atherosclerosis of the coronary arteries commonly causes coronary artery disease, myocardial infarction, coronary thrombosis, and angina pectoris. Atherosclerosis of the arteries supplying the central nervous system frequently provokes strokes and transient cerebral ischemia. In the peripheral circulation, atherosclerosis causes intermittent claudication and gangrene and can jeopardize limb viability. Atherosclerosis of an artery of the splanchnic circulation can cause mesenteric ischemia. Atherosclerosis can also affect the kidneys directly (e.g., renal artery stenosis).

A patient who is being treated for an atherosclerosis-associated disease is one who a medical practitioner has diagnosed as having such a disease. Diagnosis may be by any suitable means. Methods for diagnosing atherosclerosis by measuring systemic inflammatory markers are described, for example, in U.S. Pat. No. 6,040,147, hereby incorporated by reference. Diagnosis and monitoring may employ an electrocardiogram, chest X-ray, echocardiogram, cardiac catheterization, ultrasound (for the measurement of vessel wall thickness), or measurement of blood levels of CPK, CPK-MB, myoglobin, troponin, homocysteine, or C-reactive protein. A patient in whom the development of an atherosclerosis-associated disease is being prevented is one who has not received such a diagnosis. One in the art will understand that these patients may have been subjected to the same tests (electrocardiogram, chest X-ray, etc.) or may have been identified, without examination, as one at high risk due to the presence of one or more risk factors (e.g., family history, hypertension, diabetes mellitus, high cholesterol levels). Thus, prophylactic administration of a sulfhydryl rifamycin compound is considered to be preventing the development of an atherosclerosis-associated disease.

An atherosclerosis-associated disease has been treated or prevented when one or more tests of the disease (e.g., any of the those described above) indicate that the patient's condition has improved or the patient's risk reduced. In one example, a reduction in C-reactive protein to normal levels indicates that an atherosclerosis-associated disease has been treated or prevented.

An alternative means by which treatment or prevention is assessed includes determination of the presence of an infection of *C. pneumoniae*. Any suitable method may be employed (e.g., determination of *C. pneumoniae* in blood monocytes or in the atheroma itself (e.g., in macrophages or foam cells present in the fatty streak), or detection of *C. pneumoniae* DNA, RNA, or antibodies to *C. pneumoniae* in a biological sample from the patient).

By "debris" is meant the mucoid exudate or desquamated epithelium in an infected ear of a patient having an ear infection.

By "ear wick" is meant a sponge, cotton, gauze, compressed hydroxycellulose, or any other material used to increase the penetration of rifamycin to the infected otic area. The ear wick is typically inserted into the canal under direct vision. Its presence helps wick eardrops along the canal, hold the solution in contact with the skin of the canal, and apply pressure to the canal skin.

By "granulation tissue" is meant the highly vascularized tissue that replaces the initial fibrin clot in a wound. Vascularization is a result of an ingrowth of capillary endothelium from the surrounding vasculature. The tissue is also rich in fibroblasts and leucocytes.

"Antibiotic-associated bacterial diarrhea" means the condition wherein antibiotic therapy disturbs the balance of the microbial flora of the gut, allowing pathogenic organisms such as *C. difficile* to flourish. These organisms cause diarrhea. Antibiotic-associated bacterial diarrhea includes such conditions as *C. difficile* associated diarrhea (CDAD) and pseudomembranous colitis.

"Pseudomembranous colitis," also known as pseudomembranous enterocolitis or enteritis, means the inflammation of the mucous membrane of both small and large intestine with the formation and passage of pseudomembranous material (composed of fibrin, mucous, necrotic epithelial cells and leukocytes) in the stools.

By "autoimmune disease" is meant a disease arising from an immune reaction against self-antigens and directed against the individual's own tissues. Examples of autoimmune diseases include but are not limited to systemic lupus erythematosus, rheumatoid arthritis, myasthenia gravis, and Graves' disease.

By "bacteria" is meant a unicellular prokaryotic microorganism that usually multiplies by cell division.

By "bacteria capable of establishing a cryptic phase" is meant any species whose life cycle includes a persistent, non-replicating, metabolically inactive phase. These species include but are not limited to *C. trachomatis*, *C. pneumo-*

*niae, C. psittaci, C. suis, C. pecorum, C. abortus, C. caviae, C. felis, C. muridarum, N. hartmannellae, W. chondrophila, S. negevensis, and P. acanthamoeba*, as well as any other species described in Everett et al. (Int. J. Syst. Evol. Microbiol. 49:415–440, 1999), incorporated herein by reference.

By "bacterial infection" is meant the invasion of a host animal by pathogenic bacteria. For example, the infection may include the excessive growth of bacteria that are normally present in or on the body of an animal or growth of bacteria that are not normally present in or on the animal. More generally, a bacterial infection pan be any situation in which the presence of a bacterial population(s) is damaging to a host animal. Thus, an animal is "suffering" from a bacterial infection when an excessive amount of a bacterial population is present in or on the animal's body, or when the presence of a bacterial population(s) is damaging the cells or other tissue of the animal.

By "chronic disease" is meant a disease that is inveterate, of long continuance, or progresses slowly, in contrast to an acute disease, which rapidly terminates. A chronic disease may begin with a rapid onset or in a slow, insidious manner but it tends to persist for several weeks, months or years, and has a vague and indefinite termination.

By "cryptic phase" is meant the latent or dormant intracellular phase of infection characterized by little or no metabolic activity. The non-replicating cryptic phase is often characteristic of persistent forms of intracellular bacterial infections.

By "elementary body phase" is meant the infectious phase of the bacterial life cycle which is characterized by the presence of elementary bodies (EBs). EBs are small (300–400 nm), infectious, spore-like forms which are metabolically inactive, non-replicating, and found most often in the acellular milieu. EBs possess a rigid outer membrane which protects them from a variety of physical insults such as enzymatic degradation, sonication and osmotic pressure.

By "immunocompromised" is meant a person who exhibits an attenuated or reduced ability to mount a normal cellular or humoral defense to challenge by infectious agents, e.g., viruses, bacterial, fungi, and protozoa. Persons considered immunocompromised include malnourished patients, patients undergoing surgery and bone narrow transplants, patients undergoing chemotherapy or radiotherapy, neutropenic patients, HIV-infected patients, trauma patients, burn patients, patients with chronic or resistant infections such as those resulting from myelodysplastic syndrome, and the elderly, all of who may have weakened immune systems.

By "inflammatory disease" is meant a disease state characterized by (1) alterations in vascular caliber that lead to an increase in blood flow, (2) structural changes in the microvasculature that permit the plasma proteins and leukocytes to leave the circulation, and (3) emigration of the leukocytes from the microcirculation and their accumulation in the focus of injury. The classic signs of acute inflammation are erythema, edema, tenderness (hyperalgesia), and pain. Chronic inflammatory diseases are characterized by infiltration with mononuclear cells (e.g., macrophages, lymphocytes, and plasma cells), tissue destruction, and fibrosis. Non-limiting examples of inflammatory disease include asthma, coronary artery disease, arthritis, conjunctivitis, lymphogranuloma venerum, and salpingitis.

By "intracytoplasmic inclusion" is meant a replicating reticulate body (RB) that has no cell wall. Such inclusions may be detected, for example, through chlamydiae sample isolation and propagation on a mammalian cell lines, followed by fixing and staining using one of a variety of staining methods including Giemsa staining, iodine staining, and immunofluorescence. These inclusions have a typical round or oval appearance.

By "persistent bacterial infection" is meant an infection that is not completely eradicated through standard treatment regimens using anti-bacterial agents. Persistent bacterial infections are caused by bacteria capable of establishing a cryptic or latent phase of infection and may be classified as such by culturing the bacteria from a patient and demonstrating bacterial survival in vitro in the presence of anti-bacterial agents or by determination of anti-bacterial treatment failure in a patient. As used herein, a persistent infection in a patient includes any recurrence of chlamydial infection, after receiving anti-bacterial treatment, from the same species (e.g., *C. trachomatis*) more than two times over the period of two or more years or the detection of the cryptic phase of the infection in the patient by the methods described. An in vivo persistent infection can be identified through the use of a reverse transcriptase polymerase chain reaction (RT-PCR) to demonstrate the presence of 16S rRNA transcripts in bacterially infected cells after treatment with anti-bacterial agents (Antimicrob. Agents Chemother. 12:3288–3297, 2000).

By "replicating phase" is meant the phase of the bacterial cell cycle characterized by the presence of an RB. The RB is the actively replicating form of the Chlamydia. It contains no cell wall and is detected as an inclusion in the cell.

As used herein, the term "treating" refers to administering a pharmaceutical composition for prophylactic and/or therapeutic purposes. To "prevent disease" refers to prophylactic treatment of a patient who is not yet ill, but who is susceptible to, or otherwise at risk of, a particular disease. To "treat disease" or use for "therapeutic treatment" refers to administering treatment to a patient already suffering from a disease to improve the patient's condition. Thus, in the claims and embodiments, treating is the administration to an animal either for therapeutic or prophylactic purposes. An ear infection has been treated when one or more tests of the disease (e.g., any of the those described below) indicate that the patient's condition has improved. The detection of an infection may be done by a pneumatic otoscopic examination of the patient, or by a reduction in infection-associated symptoms in the patient (e.g., inflammation of ear drums, redness of ear drums, presence of fluid in ears). Reduction of symptoms may also be determined, for example, by audiogram to check recovery from hearing loss. Prophylactic administration of a rifamycin of the invention is considered to be preventing the development of an ear infection.

By "effective amount" is meant the amount of a compound required to treat or prevent an infection. The effective amount of active compound(s) used to practice the present invention for therapeutic or prophylactic treatment of conditions caused by or contributed to by a microbial infection varies depending upon the manner of administration, the age, body weight, and general health of the subject. Ultimately, the attending physician or veterinarian will decide the appropriate amount and dosage regimen. Such amount is referred to as an "effective" amount.

The term "microbial infection" refers to the invasion of the host animal by pathogenic microbes. This includes the excessive growth of microbes that are normally present in or on the body of an animal. More generally, a microbial infection can be any situation in which the presence of a microbial population(s) is damaging to a host animal. Thus, an animal is "suffering" from a microbial infection when excessive numbers of a microbial population are present in or on an animal's body, or when the presence of a microbial population(s) is damaging the cells or other tissue of an animal.

The term "microbes" includes, for example, bacteria, fungi, yeasts, viruses and protozoa.

By "intracellular pathogen" is meant an infection by any facultative or obligate intracellular microbe.

By "obligate intracellular pathogen" is meant a microbe which must use an intracellular location (e.g., a host cell) in order to replicate.

By "facultative intracellular pathogen" is meant a microbe which is able to survive within an intracellular location (e.g., a host cell), but does not require an intracellular environment to replicate.

The term "administration" or "administering" refers to a method of giving a dosage of a pharmaceutical composition to an animal, where the method is, e.g., topical, oral, intravenous, intraperitoneal, or intramuscular. The preferred method of administration can vary depending on various factors, e.g., the components of the pharmaceutical composition, site of the potential or actual disease, and severity of disease.

The terms "animal," "subject," and "patient" specifically include humans, cattle, horses, dogs, cats, and birds, but also includes many other species.

DETAILED DESCRIPTION

Figure 1:
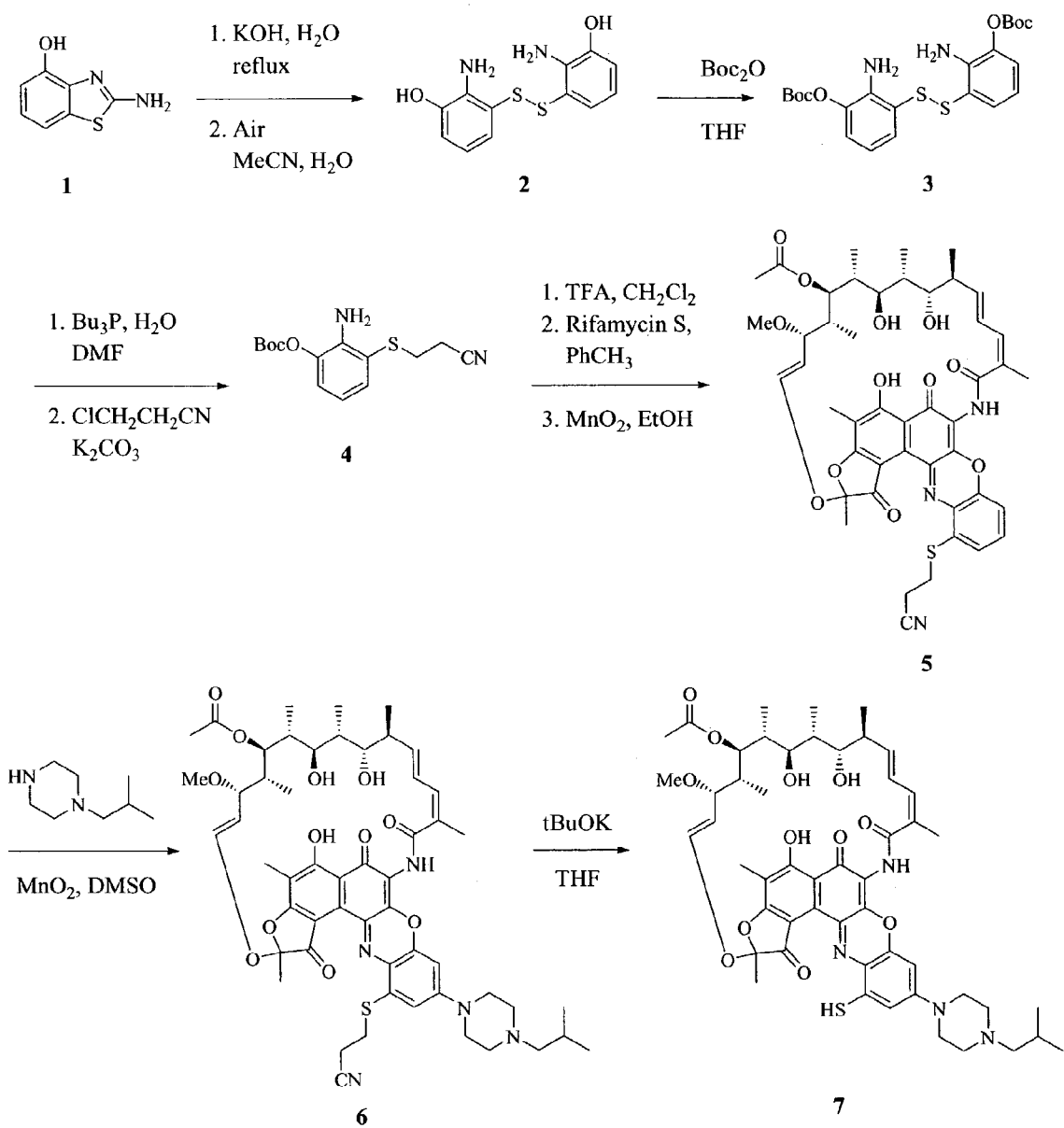
FIG. 1 is a synthetic scheme depicting the synthesis of compound 7.

We have discovered that sulfhydryl rifamycin compounds are useful for treating or preventing a variety of microbial infections. The compounds of the present invention are described by formula I:

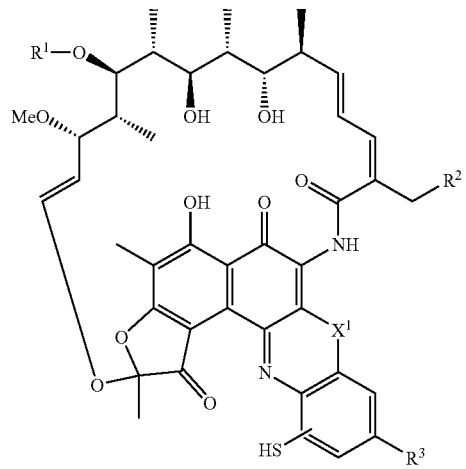

I

In formula I, $X^1$ represents an oxygen atom or a sulfur atom, $R^1$ represents a hydrogen or an acetyl group, $R^2$ represents a hydrogen or hydroxyl group, and $R^3$ represents a hydrogen atom or a group expressed by the formula:

wherein each of $R^4$ and $R^5$ is, independently, an alkyl group having 1 to 7 carbon atoms, or $R^4$ and $R^5$ combine to form a 3–8 membered cyclic system, or $R^3$ represents a group expressed by the formula:

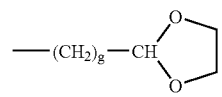

in which g represents an integer between 1 and 3;

or $R^3$ represents a group expressed by the formula:

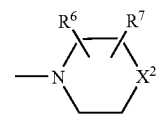

wherein each of $R^6$ and $R^7$ is, independently, a hydrogen atom or an alkyl group having 1 to 3 carbon atoms, $X^2$ represents an oxygen atom, a sulfur atom, or a carbonyl group, or $X^2$ represents a group expressed by the formula:

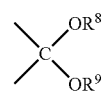

in which each of $R^8$ and $R^9$ is, independently, a hydrogen atom, or an alkyl group having 1 to 3 carbon atoms, or $R^8$ and $R^9$, in combination with each other, represent —$(CH_2)_k$— in which k represents an integer between 1 and 4;

or $X^2$ represents a group expressed by the formula:

in which m represents 0 or 1, $R^{10}$ represents a hydrogen atom, an alkyl group having 1 to 6 carbon atoms, or —$(CH^2)_n X^3$ in which n represents an integer between 1 and 4, and $X^3$ represents an alkoxy group having 1 to 3 carbon atoms, a vinyl group, an ethynyl group, or $X^2$ represents a group expressed by the formula:

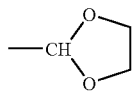

We have identified a method of preventing, stabilizing, or inhibiting the growth of microbes, or killing microbes. The method involves contacting microbes or a site susceptible to microbial growth with a compound of the invention. Compounds of the present invention can be used to treat, stabilize or prevent a microbial infection in an animal. In this method, the step of contacting microbes or a site susceptible to microbial infection (e.g., a site in or on the body of an animal) with a compound of the invention includes administering to the animal the compound in an amount sufficient to treat, stabilize, or prevent the microbial infection in the animal.

In particular embodiments, compounds of the present invention can be used to treat atherosclerosis or diseases associated therewith, sexually transmitted diseases caused, for example, by *C. trachomatis* or *N. gonorrhoeae*, otitis media and other ear infections, antibiotic-associated colitis, gastritis and ulcers associated with an infection of *H. pylori*, community-acquired pneumonia, upper and lower respiratory tract infections, skin and soft tissue infections, bone and joint infections, hospital-acquired lung infections, urinary tract infections, pyelonephritis, intra-abdominal infections, bacterial sepsis, would infections, peritonitis, osteomyelitis, infections after burns, pelvic inflammatory disease, and diseases associated with chronic infections.

Atherosclerosis and Other Diseases Associated with Chlamydial Infection

An association was previously reported in International Publication No. WO 98/50074 between the cryptic phase of a persistent chlamydial infection of body fluids and/or tissues and several chronic disease syndromes of previously unknown etiology in humans. To date, these diseases include, but are not limited to, atherosclerosis, multiple sclerosis, rheumatoid arthritis, inflammatory bowel disease, interstitial cystitis, fibromyalgia, autonomic nervous dysfunction (neural-mediated hypotension); pyoderma gangrenosum, and chronic fatigue syndrome.

As described in International Publication No. WO 98/50074, several lines of evidence have led to the establishment of a link between *Chlamydia* and a broad set of inflammatory, autoimmune, and immune deficiency diseases. These include (i) the association between the cryptic phase of a persistent chlamydial infection of body fluids and/or tissues and several chronic disease syndromes as described above, (ii) published evidence of an association between atherosclerosis and *Chlamydia* (Circulation, 96:404–407, 1997), and (iii) an understanding of the impact the persistent infection established by the cryptic phase of chlamydial infections can have on infected cells and the immune system. Thus, the present invention describes methods for treating chronic diseases associated with the cryptic phase of a persistent chlamydial infection, such as autoimmune diseases, inflammatory diseases and diseases that occur in immuno-compromised individuals by treating the cryptic phase of the infection in an individual in need thereof, using the sulfhydryl rifamycins described herein. Progress of the treatment can be evaluated, using the diagnostic tests described herein, to determine the presence or absence of *Chlamydia*. Physical improvement in the conditions and symptoms typically associated with the disease to be treated can also be evaluated. Based upon these evaluating factors, the physician can maintain or modify the anti-bacterial therapy accordingly.

The therapies described herein can be used for the treatment of chronic immune and autoimmune diseases when patients are demonstrated to have a *Chlamydia* load by the methods of detection described above. These diseases include, but are not limited to, chronic hepatitis, systemic lupus erythematosus, arthritis, thyroidosis, scleroderma, diabetes mellitus, Graves' disease, Beschet's disease, and graft versus host disease (graft rejection). The therapies of this invention can also be used to treat any disorders in which a chlamydial species is a factor or co-factor.

Thus, the present invention can be used to treat a range of disorders in addition to the above immune and autoimmune diseases when demonstrated to be associated with chlamydial infection by the methods of detection described herein; for example, various infections, many of which produce inflammation as primary or secondary symptoms, including, but not limited to, sepsis syndrome, cachexia, circulatory collapse and shock resulting from acute or chronic bacterial infection, acute and chronic parasitic and/or infectious diseases from bacterial, viral or fungal sources, such as a HIV, AIDS (including symptoms of cachexia, autoimmune disorders, AIDS dementia complex and infections) can be treated, as well as Wegners Granulomatosis.

Among the various inflammatory diseases, there are certain features that are generally agreed to be characteristic of the inflammatory process. These include fenestration of the microvasculature, leakage of the elements of blood into the interstitial spaces, and migration of leukocytes into the inflamed tissue. On a macroscopic level, this is usually accompanied by the familiar clinical signs of erythema, edema, tenderness (hyperalgesia), and pain. Inflammatory diseases, such as chronic inflammatory pathologies and vascular inflammatory pathologies, including chronic inflammatory pathologies such as aneurysms, hemorrhoids, sarcoidosis, chronic inflammatory bowel disease, ulcerative colitis, and Crohn's disease and vascular inflammatory pathologies, such as, but not limited to, disseminated intravascular coagulation, atherosclerosis, and Kawasaki's pathology are also suitable for treatment by methods described herein. The invention can also be used to treat inflammatory diseases such as coronary artery disease, hypertension, stroke, asthma, chronic hepatitis, multiple sclerosis, peripheral neuropathy, chronic or recurrent sore throat, laryngitis, tracheobronchitis, chronic vascular headaches (including migraines, cluster headaches and tension headaches) and pneumonia.

Treatable disorders when associated with a chlamydial infection also include, but are not limited to, neurodegenerative diseases, including, but not limited to, demyelinating diseases, such as multiple sclerosis and acute transverse myelitis; extrapyramidal and cerebellar disorders, such as lesions of the corticospinal system; disorders of the basal ganglia or cerebellar disorders; hyperkinetic movement disorders such as Huntington's Chorea and senile chorea; drug-induced movement disorders, such as those induced by drugs which block CNS dopamine receptors; hypokinetic movement disorders, such as Parkinson's disease; progressive supranucleo palsy; cerebellar and spinocerebellar disorders, such as astructural lesions of the cerebellum; spinocerebellar degenerations (spinal ataxia, Friedreich's ataxia, cerebellar cortical degenerations, multiple systems degenerations (Mencel, Dejerine-Thomas, Shi-Drager, and Machado Joseph)); and systemic disorders (Refsum's disease, abetalipoprotemia, ataxia, telangiectasia, and mitochondrial multi-system disorder); demyelinating core disorders, such as multiple sclerosis, acute transverse myelitis; disorders of the motor unit, such as neurogenic muscular atrophies (anterior horn cell degeneration, such as amyotrophic lateral sclerosis, infantile spinal muscular atrophy and juvenile spinal muscular atrophy); Alzheimer's disease; Down's Syndrome in middle age; Diffuse Lewy body disease; senile dementia of Lewy body type; Wernicke-Korsakoff syndrome; chronic alcoholism; Creutzfeldt-Jakob disease; subacute sclerosing panencephalitis, Hallerrorden-Spatz disease; and Dementia pugilistica, or any subset thereof.

It is also recognized that malignant pathologies involving tumors or other malignancies, such as, but not limited to leukemias (acute, chronic myelocytic, chronic lymphocytic and/or myelodyspastic syndrome); lymphomas (Hodgkin's and non-Hodgkin's lymphomas, such as malignant lymphomas (Burkitt's lymphoma or mycosis fungoides)); carcinomas (such as colon carcinoma) and metastases thereof; cancer-related angiogenesis; infantile hemangiomas; and alcohol-induced hepatitis. Ocular neovascularization, psoriasis, duodenal ulcers, angiogenesis of the female reproductive tract, can also be treated when demonstrated by the diagnostic procedures described herein to be associated with a chlamydial infection.

Ear Infections

Ear infections typically affect the middle or the external ear and include, for example, otitis media, otitis externa, and infections caused by surgical interventions. Due to multiplicity of secondary complications that arise from ear infections such as hearing loss, the treatment and prevention of such conditions is critical.

Topical administration of a sulfhydryl rifamycin compound of formula I is effective in treating or preventing an infection of the ear, such as otitis media or otitis externa. In the case of otitis media or externa, infections are primarily caused by *H. influenza, M. catarhalis, S. pneumoniae, S. pyogenes, S. intermedius, S. epidermidis, S. aureus, S. caprae, S. auriculis, S. capitis, S. haemolytis, P. aeroginosa, P. mirabilis, P. vulgaris, E. faecalis,* or *E. coli*. A sulfhydryl rifamycin compound of formula I can be used to treat each of these infections of the ear. The sulfhydryl rifamycin compound of formula I may, for example, be topically administered to the area of the ear to which surgical intervention was performed or, alternatively, the rifamycin may be administered to the ear of the patient prophylactically, prior to otic surgery, noninvasive otic procedures, or other types of surgery. Exemplary surgical procedures include for example, cochlear implant surgery, tympanoplasty, tympanostomy tube insertion, removal of tumors (e.g., cholesteatoma), or stapedectomy. The compound may be administered to the area of the ear to which surgical intervention will be performed, for example, within seven days, two days, one day, 12 hours, 10 hours, 6 hours, 4 hours, 2 hours, 1 hour, or less than 1 hour prior to or following the surgical intervention. The compositions may be used for acute treatment of temporary conditions, or may be administered chronically.

A sulfhydryl rifamycin compound of formula I may be given daily (e.g., once, twice, three times, or four times daily) or less frequently (e.g., once every other day, or once or twice weekly). Typically, patients are administered a dosage consisting of one to four drops of solution containing the compound. The compound may be contained in any appropriate amount in any suitable carrier substance, and is generally present in an amount between 0.001% and 5%, desirably 0.01% and 3%, more desirably 0.1% and 1%, and even more desirably 0.1% and 0.4% by weight of the total volume (w/v) of the composition. The compound is provided in a dosage form that is suitable for topical administration. Thus, a composition containing a sulfhydryl rifamycin compound of formula I may be in the form of a solution, aerosol, gel, ointment, nebulizer, or suspension. Alternatively, the rifamycin may be administered by placing an impregnated porous media into the external ear canal to the tympanic membrane. The pharmaceutical composition can generally be formulated according to conventional pharmaceutical practice.

Aural Toilet

The external auditory canal and tissues lateral to the infected middle ear often are covered with mucoid exudate or desquamated epithelium. Since topically applied preparations cannot generally penetrate affected tissues until these interposing materials are removed, aural toilet is desirably performed before administering a sulfhydryl rifamycin compound of formula I. Aural toilet may be performed by a health provider, the patient, or any other individual. Removal of debris may be performed mechanically with the assistance of a microscope and microinstruments. Aural irrigation may also be performed using a solution containing peroxide. The concentration of peroxide should be the highest concentration without causing significant pain, or discomfort, to the patient. As an example, a solution of 50% peroxide and 50% sterile water can be used. Thirty to 40 mL of this solution can be irrigated through the external auditory canal, using a small syringe or bulb-type aspirator. The irrigant solution is allowed to drain out (e.g., for 5–10 minutes) prior to administering a rifamycin of the present invention.

Granulation Tissue

Granulation tissue often fills the middle ear and medial portions of the external auditory canal, and reducing this accumulation is beneficial for resolution of an ear infection. Granulation tissue may also prevent topically applied antimicrobial agents from penetrating to the site of infection, and the amount of granulation tissue is desirably reduced throughout the regimen. Although topical antimicrobial drops can reduce granulation by eliminating infection and by removing the inciting irritating inflammation, the amount of granulation tissue ay be reduced using other methods known in the art. For example, topical steroids may hasten the resolution of middle ear granulation, thus improving penetration of topically delivered antibiotics.

Cautery may also be used to reduce the amount of granulation tissue and to reduce its formation. Microbipolar cautery may be administered by a health provider. Chemical cautery, using for example silver nitrate, may also be applied to an infected ear in the form of silver nitrate sticks. Excision of granulation tissue may also be performed by a health care provider with a microscope and microinstruments.

Ear Canal Acidification

In a patient affected with otitis externa, a therapy involving ear canal acidification to restore the physiological acidity of the ear may be performed. The affected ear is administered with a solution containing acetic acid, which may also include a steroid (e.g., hydrocortisone), aluminum acetate, or rubbing alcohol.

Topical Formulations

Pharmaceutical compositions according to the present invention can be formulated for topical administration to the ear of the patient. Patients having an ear infection may be administered with effective amounts of the rifamycin of the invention, by means of a solution (e.g., drops), ointment, gel, or aerosol (e.g., nebulizer). The composition is typically administered to the affected otic area by topically applying, for example, one to four drops of a solution or suspension, or a comparable amount of an ointment, gel, or other solid or semisolid composition, once, twice, three times, or more than three times per day. A porous media or an ear wick (e.g., cotton, gauze, or compressed hydroxycellulose) may also be used to increase the penetration of the rifamycin to the infected otic area. The ear wick, which is inserted into the canal under direct vision, is typically a dried sponge that helps wick eardrops along the canal, hold the solution in contact with the skin of the canal and apply pressure to the canal skin. Wicks may be removed at one day, two days, or more than two days, and may be replaced if necessary. Alternatively, the ear wick may itself be impregnated with the rifamycin. These formulations can be made according to known and conventional methods for preparing such formulations.

Since some of the sulfhydryl rifamycin compounds of formula I of this invention may not be highly soluble in water at physiological conditions, a solubilizing excipient may be used to increase solubility. Solubilization is taken to mean an improvement in the solubility by virtue of surface-active compounds that can convert substances that are insoluble or virtually insoluble in water into clear, or opalescent, aqueous solutions without changing the chemical structure of these substances in the process. Excipients used for this purpose are restricted to those that are safe for administration to humans. Typically such co-solvents are employed at a level of about 0.01% to 2% by weight.

A variety of solubilizing excipients may be used for the formulation of the rifamycin, including compounds belonging to the following classes: polyethoxylated fatty acids, PEG-fatty acid diesters, PEG-fatty acid mono-ester and di-ester mixtures, polyethylene glycol glycerol fatty acid esters, alcohol-oil transesterification products, polyglycerized fatty acids, propylene glycol fatty acid esters, mixtures of propylene glycol esters and glycerol esters, mono- and diglycerides, sterol and sterol derivatives, polyethylene glycol sorbitan fatty acid esters, polyethylene glycol alkyl ethers, sugar esters, polyethylene glycol alkyl phenols, polyoxyethylene-polyoxypropylene block copolymers, sorbitan fatty acid esters, lower alcohol fatty acid esters, or ionic surfactants. Such excipients are described for example, in U.S. patent application Ser. No. 60/385,532, hereby incorporated by reference.

Ototopical preparations may vary in viscosity. The use of viscosity enhancing agents to provide the compositions of the invention with viscosities greater than the viscosity of simple aqueous solutions may be desirable to increase the retention time in the ear. Such viscosity-building agents include, for example, polyvinyl alcohol, polyvinyl pyrrolidone, methyl cellulose, hydroxypropyl methylcellulose, hydroxyethyl cellulose, carboxymethyl cellulose, hydroxypropyl cellulose, or other agents known to those skilled in the art. Such agents are typically employed at a level of about 0.01% to 2% by weight. Optionally, these preparations may include a buffering agent to maintain an acidic pH, since the normal environment of the external auditory canal is acidic. However, if treatment is required in the middle ear where the pH is neutral, the pH can be adjusted accordingly.

Otic pharmaceutical products are typically packaged in multidose form. Preservatives are thus desired to prevent microbial contamination during use. Suitable preservatives include: polyquaternium-1, benzalkonium chloride, thimerosal, chlorobutanol, methyl paraben, propyl paraben, phenylethyl alcohol, edetate disodium, sorbic acid, or other agents known to those skilled in the art. Typically such preservatives are employed at a level of from 0.001% to 1.0% by weight.

A penetration enhancer may also be used to facilitate the diffusion of the rifamycin through the tympanic membrane into the middle and inner ear in order to reduce inflammation of ear tissues. A penetration enhancer is an agent used to increase the permeability of the skin to a pharmacologically active agent to increase the rate at which the drug diffuses through the skin and enters the tissues and bloodstream. A chemical skin penetration enhancer increases skin permeability by reversibly damaging or by altering the physiochemical nature of the stratum corneum to reduce its diffusional resistance (Osborne D W, Henke J J, Pharmaceutical Technology, November 1997, pp 58–86). Examples of penetration enhancers include without limitation: alcohols, such as ethanol and isopropanol; polyols, such as n-alkanols, limonene, terpenes, dioxolane, propylene glycol, ethylene glycol, other glycols, and glycerol; sulfoxides, such as dimethylsulfoxide (DMSO), dimethylformamide, methyl dodecyl sulfoxide, dimethylacetamide; esters, such as isopropyl myristate/palmitate, ethyl acetate, butyl acetate, methyl proprionate, and capric/caprylic triglycerides; ketones; amides, such as acetamides; oleates, such as triolein; various surfactants, such as sodium lauryl sulfate; various alkanoic acids, such as caprylic acid; lactam compounds, such as azone; alkanols, such as oleyl alcohol; dialkylamino acetates, and admixtures thereof. The use of such penetration enhancers is disclosed, for example, in U.S. Pat. No 6,093,417, hereby incorporated by reference.

Other Therapeutic Agents

Preparations containing a sulfhydryl rifamycin of the present invention may also include a second therapeutic agent, including for example, another rifamycin, an anesthetic, an antimicrobial agent, a zinc salt, or an anti-inflammatory agent (e.g., an non-steroidal anti-inflammatory or a steroid). When admixing an antimicrobial agent, the antimicrobial agent is preferably amoxillin, erythromycin, azithromycin, clarithromycin, gentamicin, tobramycin, ciprofloxaxin, norfloxacin, gatifloxacin, ofloxacin, levofloxacin, moxifloxacin, metronidazole, lomefloxacin, ciprofloxacin, natamycin, neomycin, polymyxin B, gentamycin, bacitracin, trovafloxacin, grepafloxacin, sulfacetamide, tetracycline, gramicidin, chloremphenicol, or gramicidin. Preferred non-steroidal anti-inflammatory agents include, for example, detoprofen, diclofenac, diflunisal, etodolac, fenoprofen, flurbiprofen, indomethacin, ketoprofen, mechlofenameate, mefenamic acid, meloxicam, nabumeone, naproxen sodium, oxaprozin, piroxicam, sulindac, tolmeting, celecoxib, rofecoxib, choline salicylate, salsate, sodium salicylate, magnesium salicylate, aspirin, ibuprofen, paracetamol, acetaminophen, and pseudoephedrine, and preferred steroids include, for example, hydrocortisone, prednisone, fluprednisolone, triamcinolone, dexamethasone, betamethasone, cortisone, prednilosone, methylprednisolone, fluocinolone acetonide, flurandrenolone acetonide, and fluorometholone. Preferred anesthetics according to the invention include, for example, benzocaine, butamben picrate, tetracaine, dibucaine, prilocaine, etidocaine, mepivacaine, bupivicaine, and lidocaine. A zinc salt can be zinc sulfate, zinc chloride, zinc acetate, zinc phenol sulfonate, zinc borate, zinc bromide, zinc nitrate, zinc glycerophosphate, zinc benzoate, zinc carbonate, zinc citrate, zinc hexafluorosilicate, zinc diacetate trihydrate, zinc oxide, zinc peroxide, zinc salicylate, zinc silicate, zinc stannate, zinc tannate, zinc titanate, zinc tetrafluoroborate, zinc gluconate, or zinc glycinate. All of the therapeutic agents employed in the compositions of the present invention can be used in the dose ranges currently known and used for these agents. Different concentrations may be employed depending on the clinical condition of the patient, the goal of therapy (treatment or prophylaxis), the anticipated duration, and the severity of the infection for which a sulfhydryl rifamycin compound of the invention is being administered. Additional considerations in dose selection include the type of infection, age of the patient (e.g., pediatric, adult, or geriatric), general health, and comorbidity.

Synthesis

Sulfhydryl rifamycin compounds of formula I can be synthesized by methods analogous to those disclosed in U.S. Pat. Nos. 4,690,919, 4,983,602, 5,786,349, 5,981,522, and 4,859,661, and Chem. Pharm. Bull., 41:148, 1993, each of which is hereby incorporated by reference. The synthesis of sulfhydryl rifamycin compounds of formula I are provided in the Examples.

Assays

Compounds of the present invention can be screened for antimicrobial activity by measuring their minimum inhibitory concentration (MIC), using standard MIC in vitro assays (see, for example, Tomioka et al., Antimicrob. Agents Chemother. 37:67, 1993). Agents can be screened against *C. pneumoniae*, *C. trachomatis*, *M. tuberculosis* (including multiple drug resistant strains), *M. avium* complex, and other intracellular infectious microbes. Details of a standard MIC assay are provided in Example 2.

Therapy

The invention features a method of treating or preventing a disease or condition associated with a microbial infection by administering a compound of formulas I or II. Compounds of the present invention may be administered by any appropriate route for treatment or prevention of a disease or condition associated with a microbial infection, inflammation, or infection derived autoimmune disease. These may be administered to humans, domestic pets, livestock, or other animals with a pharmaceutically acceptable diluent, carrier, or excipient, in unit dosage form. Administration may be topical, parenteral, intravenous, intra-arterial, subcutaneous, intramuscular, intracranial, intraorbital, ophthalmic, intraventricular, intracapsular, intraspinal, intracisternal, intraperitoneal, intranasal, aerosol, by suppositories, or oral administration.

Therapeutic formulations may be in the form of liquid solutions or suspensions; for oral administration, formulations may be in the form of tablets or capsules; and for intranasal formulations, in the form of powders, nasal drops, or aerosols.

Methods well known in the art for making formulations are found, for example, in Remington: The Science and Practice of Pharmacy (20th ed., ed. A. R. Gennaro AR.), Lippincott Williams & Wilkins, 2000. Formulations for parenteral administration may, for example, contain excipients, sterile water, or saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Nanoparticulate formulations (e.g., biodegradable nanoparticles, solid lipid nanoparticles, liposomes) may be used to control the biodistribution of the compounds. Other potentially useful parenteral delivery systems include ethylene-vinyl acetate copolymer particles, osmotic pumps, implantable infusion systems, and liposomes. Formulations for inhalation may contain excipients, for example, lactose, or may be aqueous solutions containing, for example, polyoxyethylene-9-lauryl ether, glycholate and deoxycholate, or may be oily solutions for administration in the form of nasal drops, or as a gel. The concentration of the compound in the formulation will vary depending upon a number of factors, including the dosage of the drug to be administered, and the route of administration.

The compound may be optionally administered as a pharmaceutically acceptable salt, such as a non-toxic acid addition salts or metal complexes that are commonly used in the pharmaceutical industry. Examples of acid addition salts include organic acids such as acetic, lactic, pamoic, maleic, citric, malic, ascorbic, succinic, benzoic, palmitic, suberic, salicylic, tartaric, methanesulfonic, toluenesulfonic, or trifluoroacetic acids or the like; polymeric acids such as tannic acid, carboxymethyl cellulose, or the like; and inorganic acid such as hydrochloric acid, hydrobromic acid, sulfuric acid phosphoric acid, or the like. Metal complexes include zinc, iron, and the like.

Administration of compounds in controlled release formulations is useful where the compound of formula (I), has (i) a narrow therapeutic index (e.g., the difference between the plasma concentration leading to harmful side effects or toxic reactions and the plasma concentration leading to a therapeutic effect is small; generally, the therapeutic index, TI, is defined as the ratio of median lethal dose ($LD_{50}$) to median effective dose ($ED_{50}$)); (ii) a narrow absorption window in he gastro-intestinal tract; or (iii) a short biological half-life, so that frequent dosing during a day is required in order to sustain the plasma level at a therapeutic level.

Many strategies can be pursued to obtain controlled release in which the rate of release outweighs the rate of metabolism of the therapeutic compound. For example, controlled release can be obtained by the appropriate selection of formulation parameters and ingredients (e.g., appropriate controlled release compositions and coatings). Examples include single or multiple unit tablet or capsule compositions, oil solutions, suspensions, emulsions, microcapsules, microspheres, nanoparticles, patches, and liposomes.

Formulations for oral use include tablets containing the active ingredient(s) in a mixture with non-toxic pharmaceutically acceptable excipients. These excipients may be, for example, inert diluents or fillers (e.g., sucrose and sorbitol), lubricating agents, glidants, and antiadhesives (e.g., magnesium stearate, zinc stearate, stearic acid, silicas, hydrogenated vegetable oils, or talc).

Formulations for oral use may also be provided as chewable tablets, or as hard gelatin capsules wherein the active ingredient is mixed with an inert solid diluent, or as soft gelatin capsules wherein the active ingredient is mixed with water or an oil medium.

Pharmaceutical formulations of compounds of the invention described herein includes isomers such as diastereomers and enantiomers, mixtures of isomers, including racemic mixtures, salts, solvates, and polymorphs thereof.

Compounds of the invention may be used in combination with another antifungal, antiviral, antibacterial, or antiprotozoan compound or combinations thereof. The other agent may be employed as a supplemental antimicrobial for the purpose of broadening the activity spectrum of the therapeutics or to obtain particular effects, such as, to reduce the development of drug resistant microbes. Compounds of the invention can be used either alone or in conjunction with other pharmaceutical compounds to effectively combat a single infection. For example, compounds of the invention may be used either alone or combined with acyclovir in a combination therapy to treat HSV-1. Compounds of the invention may also be used either alone or in conjunction with other pharmaceutical compounds to combat multiple infections. For example, compounds of the invention may be used in combination with one or more anti-mycobacterial agents agents such as isoniazid, pyrazinamide, or ethambutol to treat or prevent intracellular bacterial infections. Compounds of the invention may also be used in combination with Intron A and/or a biflavanoid for treating Hepatitis B; with gancyclovir, progancyclovir, famcyclovir, foscarnet, vidarabine, cidovir, and/or acyclovir for treating herpes viruses; and with ribavarin, amantidine, and/or rimantidine for treating respiratory viruses.

The following examples are put forth so as to provide those of ordinary skill in the art with a complete disclosure and description of how the methods and compounds claimed herein are performed, made, and evaluated, and are intended to be purely exemplary of the invention and are not intended to limit the scope of what the inventors regard as their invention.

EXAMPLE 1

Synthesis of Sulfhydryl Rifamycin Compounds

Sulfhydryl rifamycin compounds can be prepared using methods which require the selective protection and deprotection of alcohols, amines, sulfhydryls and/or carboxylic acid functional groups. For example, commonly used protecting groups for amines include carbamates, such as tert-butyl, benzyl, 2,2,2-trichloroethyl, 2-trimethylsilylethyl, 9-fluorenylmethyl, allyl, and m-nitrophenyl. Other commonly used protecting groups for amines include amides, such as formamides, acetamides, trifluoroacetamides, sulfonamides, trifluoromethanesulfonyl amides, trimethylsilylethanesulfonamides, and tert-butylsulfonyl amides. Examples of commonly used protecting groups for carboxylic acids include esters, such as methyl, ethyl, tert-butyl, 9-fluorenylmethyl, 2-(trimethylsilyl)ethoxy methyl, benzyl, diphenylmethyl, O-nitrobenzyl, ortho-esters, and halo-esters. Examples of commonly used protecting groups for alcohols include ethers, such as methyl, methoxymethyl, methoxyethoxymethyl, methylthiomethyl, benzyloxymethyl, tetrahydropyranyl, ethoxyethyl, benzyl, 2-napthylmethyl, O-nitrobenzyl, P-nitrobenzyl, P-methoxybenzyl, 9-phenylxanthyl, trityl (including methoxy-trityls), and silyl ethers. Examples of commonly used protecting groups for sulfhydryls include many of the same protecting groups used for hydroxyls. In addition, sulfhydryls can be protected in a reduced form (e.g., as disulfides) or an oxidized form (e.g., as sulfonic acids, sulfonic esters, or sulfonic amides). Protecting groups can be chosen such that selective conditions (e.g., acidic conditions, basic conditions, catalysis by a nucleophile, catalysis by a lewis acid, or hydrogenation) are required to remove each, exclusive of other protecting groups in a molecule. The conditions required for the addition of protecting groups to amine, alcohol, sulfhydryl, and carboxylic acid functionalities and the conditions required for their removal are provided in detail in T. W. Green and P. G. M. Wuts, Protective Groups in Organic Synthesis ($2^{nd}$ Ed.), John Wiley & Sons, 1991 and P. J. Kocienski, Protecting Groups, Georg Thieme Verlag, 1994 (hereby incorporated by reference). In the examples that follow, the use of protecting groups is indicated in a structure by the letter P, where P for any amine, carboxylic acid, sulfhydryl, or alcohol may be any of the protecting groups listed above.

Precursor Sulfhydryl Amino Phenol

Rifamycin derivatives having the formula I in which $R^2$ is sulfhydryl may be prepared by reacting rifamycin S (LKT Laboratories, Inc., catalogue number DR32202) with a compound having the formula III.

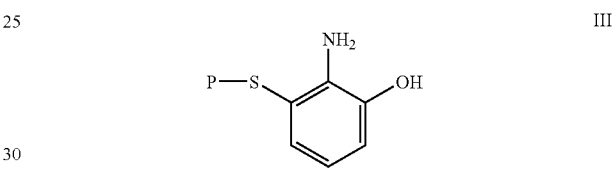

III

Compounds of formula III are prepared from 2-aminoresorcinol (Chem Service, Inc., catalogue number 1895B) as shown in reaction 1. The unprotected hydroxyl can be activated using standard techniques (e.g., conversion to a tosylate, reaction 1

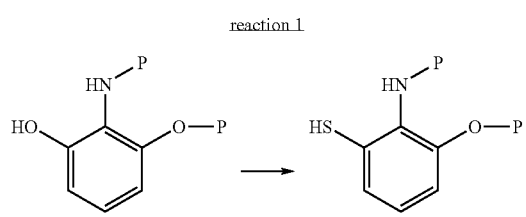

brosylate, mesylate, triflate or other reactive leaving group see, for example, J. March, Advanced Organic Chemistry: Reactions, Mechanisms and Structure, John Wiley & Sons, Inc. pp. 352–354, 1992). The conversion of the activated alcohol to a sulfhydryl group can be achieved by either addition of sulfide (e.g., NaSH, Na$_2$S), addition of disulfide (e.g., Na$_2$S$_2$) followed by reduction of the disulfide to a sulfhydryl group, or transesterification of the activated alcohol with thioacetate followed by hydrolysis to the sulfhydryl with sodium acetate. The reaction product is converted into a compound of formula III using standard protection and deprotection chemistry.

Synthesis of Sulfhydryl Rifamycin

In a typical reaction, a compound of formula III is added in small portions to a solution of rifamycin S in chloroform containing several equivalents of triethylamine. This can be followed by the addition of manganese dioxide and the reaction stirred until reaching completion. The resulting compound will have formula IV shown below.

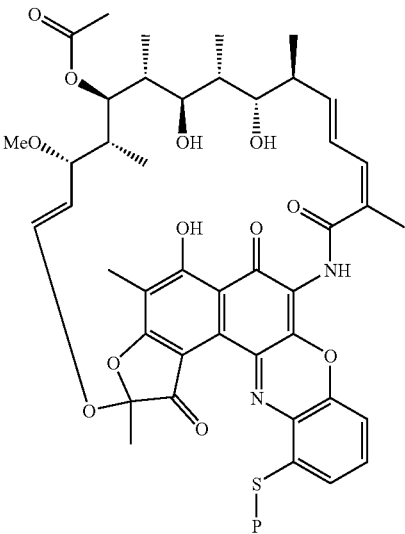

Synthesis of Sulfhydryl Rifamycin Derivatives of Formula I

The sulfhydryl rifamycin product is further modified, using the methods disclosed in U.S. Pat. No. 4,690,919. A compound represented by formula IV is dissolved in DMSO, mixed with N-isobutylpiperazine and manganese dioxide, and the reaction mixture stirred at room temperature for 3 hours. The resulting product is shown below.

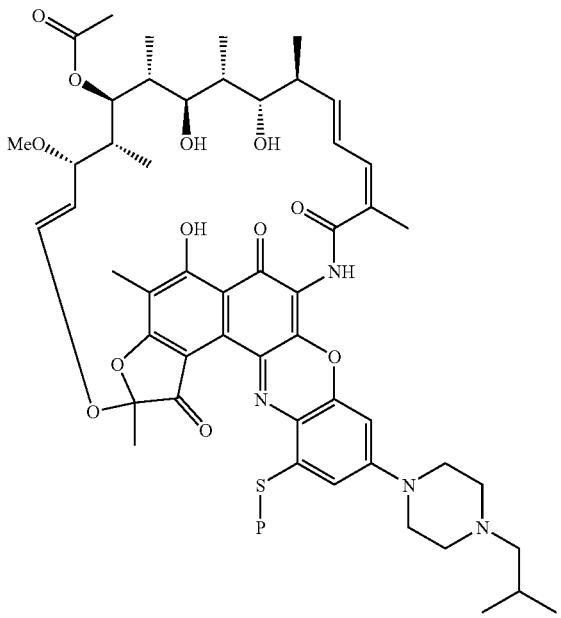

The sulfhydryl protecting group can be removed, resulting in a compound of formula I.

Compounds in which $R^3$ of formula I is selected from other groups can be prepared by an analogous method.

Synthesis of Compounds of Formula I in which $X^1$ is Sulfur

Compounds for which $X^1$ of formula I is a sulfur atom are prepared by an analogous method, but using a starting material of formula V, shown below.

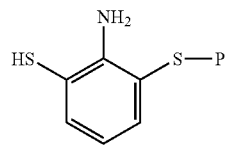

This material can also be prepared from 2-aminoresorcinol. For example, a compound of formula V can be prepared by converting both hydroxyls of 2-aminoresorcinol to sulfhydryls, vide supra, followed by the deprotection and/or protection of functional groups.

A compound of formula V can be combined with rifamycin S, vide supra, to produce the sulfhydryl rifamycin intermediate of formula VI shown below.

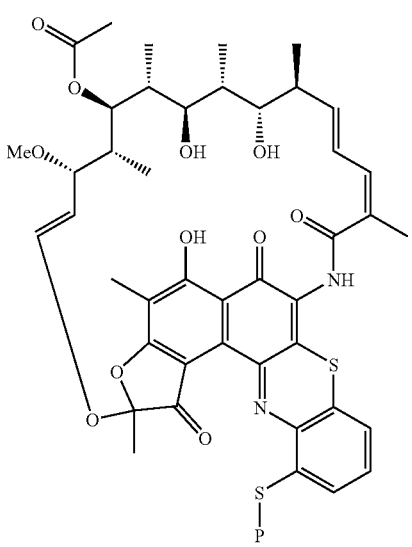

To the intermediate of formula VI may be added $R^3$, as defined in formula I, using the methods disclosed in U.S. Pat. No. 4,690,919, and described herein.

EXAMPLE 2

MIC Assay

MICs of candidate compounds of the invention can be determined, for example, by the method of Lee et al., Am. Rev. Respir. Dis. 136:349 (1987). To a BACTEC 12B vial (4 mL of 7H12B medium), 0.1 mL of a 10-fold dilution of subculture of the test organisms in 7H9 medium (optical density at 540 nm, 0.1) is inoculated and cultured at 37° C. until a growth index (GI) of 999 is reached. Then the broth culture is removed and diluted 100-fold, and 0.1 mL of the dilution is inoculated into a BACTEC 12B vial with or without a candidate compound. The candidate compound containing vials can hold 0.1 mL of candidate compound solution appropriately diluted to obtain the desired concentration. A 1% control vial, 0.L ml of the 100-fold dilution of the inoculum described above, is inoculated into 12B vial without candidate compound. The 12B vials are incubated at 37° C., and GI readings recorded daily, using a BACTEC 460 TB instrument (Johnston Laboratories, Townsend, Md.), until the control vial reaches a GI greater than 30. When the final readings in the GI of the candidate containing vials are lower than those of the 1% control, the drug is considered to have inhibited more than 99% of the bacterial population, and this concentration will be defined as the MIC.

EXAMPLE 3

Synthesis of Compound 7, a Sulfhydryl Rifamycin

Synthesis of Compound 2

Compound 1 (9.95 g, 59.9 mmol) was added to an aqueous solution of KOH (200 mL, 9 M). The reaction was stirred at reflux for 22 hours and then cooled to room temperature. The reaction was extracted once with ether, followed by acidification with 50% acetic acid (pH 5–6). The aqueous layer was extracted with methylene chloride (×5), and the combined organics were dried over $Na_2SO_4$. Filtration followed by removal of the solvent in vacuo yielded a mixture of the free thiol and 2 as a yellow solid (7.82 g) that was used with out further purification.

To a stirred solution of the above mixture (7.79 g) in acetonitrile (280 mL) and water (140 mL) was bubbled air for 32 hours. The reaction was poured over water and the aqueous layer was extracted with methylene chloride (×5). The combined organics were dried over $Na_2SO_4$ and filtered. Removal of the solvent in vacuo yielded the title compound 2 as a light-brown solid (7.46 g, 26.6 mmol, 89%, 2-step), which was used with out further purification. $^1$H NMR ($CD_3OD$, 300 MHz): 6.38–6.44 (m, 2H), 6.66–6.72 (m, 4H). ESI (+) MS: 281 (M+H$^+$).

Synthesis of Compound 3

To a stirred solution of 2 (2.33 g, 8.31 mmol) in THF (40 mL) was added di-tert-butyl dicarbonate (7.25 g, 33.2 mmol). The reaction was stirred at 50° C. for 20 hours and then cooled to room temperature. The solvent was removed in vacuo, and the resulting residue was dissolved in ethyl acetate, washed with $KHSO_4$ (0.5 M), water, brine and dried over $Na_2SO_4$. The solution was decanted, and the solvent removed in vacuo. The resulting residue was purified via flash chromatography (silica gel, methylene chloride) to yield the title compound 3 as a yellow-brown viscous oil (3.60 g, 7.49 mmol, 90%). $^1$H NMR ($CDCl_3$, 300 MHz): 1.55 (s, 18H), 4.39 (s, 4H), 6.58 (t,j=7.8 Hz, 2H), 7.06–7.11 (m, 4H). ESI (+) MS: 481 (M+H$^+$).

Synthesis of Compound 4

To a stirred solution of 3 (1.07 g, 2.23 mmol) in DMF (11 mL, sparged with $N_2$) was added water (41 µL, 2.27 mmol) and tri-n-butylphosphine (835 µL, 3.35 mmol). The reaction was stirred at room temperature under $N_2$ for 1.5 hours. 3-chloropropionitrile (350 µL, 4.46 mmol) and $K_2CO_3$ (616 mg, 4.46 mmol) were added, and the reaction was stirred at room temperature under $N_2$ for 14.5 hours. The reaction was diluted with ethyl acetate, filtered and poured over water. The organic layer was washed with water and 5% LiCl (×2), dried over $Na_2SO_4$, filtered and the solvent removed in vacuo. The resulting residue was purified using MPLC (1:1, Ethyl acetate:Hexanes) and repurified via flash chromatography (silica gel, 1:1, Ethyl acetate:Hexanes) to yield the title compound 4 as a colorless oil (534 mg, 1.81 mmol, 41%). $^1$H NMR ($CDCl_3$, 300 MHz): 1.56 (s, 9H), 2.53 (t, j=6.9 Hz, 2H), 2;96 (t,j=6.9 Hz, 2H), 4.50 (s, 2H), 6.70 (t,j=7.8 Hz, 1H), 7.14 (dd,j=1.3, 8.0 Hz, 1H), 7.29 (dd,j=1.3, 7.7 Hz, 1H). ESI (+) MS: 239 (M−tBu$^+$+2H$^+$), 195 (M−Boc$^+$+2H$^+$).

Synthesis of Compound 5

A solution of 4 (523 mg, 1.78 mmol) in methylene chloride (5 mL) and trifluoroacetic acid (5 mL) was stirred at room temperature for 2.5 hours. The solvent was removed in vacuo, and the resulting residue was dissolved in methylene chloride and washed with $NaHCO_3$ solution. The aqueous layer was extracted with methylene chloride and the combined organics were dried over $Na_2SO_4$. Filtration, followed by removal of the solvent in vacuo yielded the free amino-phenol as a white solid that was used without further purification.

A solution of the above amino-phenol and Rifamycin S (1.24 g, 1.78 mmol) in toluene (15 mL) was stirred at 50° C. under $N_2$ for 18 hours, and at 60° C. for an additional 8 hours. The reaction was cooled to room temperature and the solvent was removed in vacuo. The resulting residue was dissolved in EtOH (15 mL), and to this was added manganese dioxide (1.55 g, 17.8 mmol). The suspension was stirred at room temperature for 22 hours. The reaction was filtered through Celite, and the solvent removed in vacuo. The resulting residue was purified via MPLC (7:3, Ethyl acetate:Hexanes) to yield the title compound 5 as a red solid (656 mg, 0.754 mmol, 42%). ESI (+) MS: 838 (M−OMe$^−$), 870 (M+H$^+$), 892 (M+Na$^+$). TLC: $R_f$=0.52 (1:9, methylene chloride: ethyl acetate, Whatman MK6F, 60 angstrom).

Synthesis of Compound 6

To a stirred solution of 5 (550 mg, 0.632 mmol) in methyl sulfoxide (10 mL) was added $MnO_2$ (549 mg, 6.32 mmol) and 1-isobutylpiperazine (90 mg, 0.632 mmol), and the resulting suspension was stirred at room temperature for 39 hours. The reaction was diluted with ethyl acetate and filtered through Celite. The resulting solution was washed with water (×4) then brine, and dried over $Na_2SO_4$. Filtration, followed by removal of the solvent in vacuo yielded a blue residue that was purified via flash chromatography (silica gel, 9:1, ethyl acetate:methylene chloride). Impure material was further purified via MPLC (1:39, methanol:methylene chloride). All pure materials were pooled, and the solvent removed in vacuo to yield the title compound 6 as a blue solid (165 mg, 0.163 mmol, 26%). ESI (+) MS: 1010 (M+H$^+$). TLC: $R_f$=0.34 (1:9, methylene chloride: ethyl acetate, Whatman MK6F, 60 angstrom).

Synthesis of Compound 7

To a stirred solution of 6 (14 mg, 13.9 µmol) in THF (1 mL) at 0° C. was added potassium tert-butoxide (8 mg, 6.95 µmol). The reaction was stirred at 0° C. for 10 minutes. Acetic acid was added dropwise until the solution turned from green to blue. The reaction was diluted with ethyl acetate and washed with $NH_4Cl$ solution and water. The organics were dried over $Na_2SO_4$, decanted, and the solvent removed in vacuo. The resulting residue was purified via preparatory TLC (1:9 methanol:methylene chloride) to yield compound 7 as a blue film (6 mg, 6.27 µmol, 45%). ESI (+) MS: 957 (M+H$^+$). UV/V is: $\lambda_{max}$=582.7 nm

OTHER EMBODIMENTS

All publications and patent applications, and patents mentioned in this specification are herein incorporated by reference.

While the invention has been described in connection with specific embodiments, it will be understood that it is capable of further modifications. Therefore, this application is intended to cover any variations, uses, or adaptations of

What is claimed is:

1. A compound of formula I:

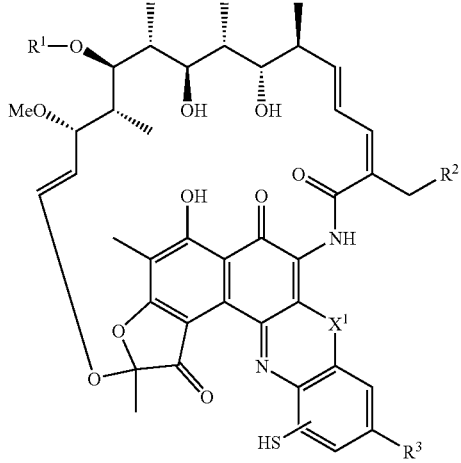

wherein
- $X^1$ represents an oxygen atom or a sulfur atom;
- $R^1$ represents a hydrogen or an acetyl group;
- $R^2$ represents a hydrogen or hydroxyl group; and
- $R^3$ represents a hydrogen atom or a group expressed by the formula:

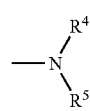

wherein each of $R^4$ and $R^5$ is, independently, an alkyl group having 1 to 7 carbon atoms, or $R^4$ and $R^5$ combine to form a 3–8 membered cyclic system, or $R^3$ represents a group expressed by the formula:

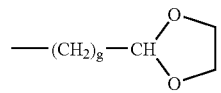

in which g represents an integer between 1 and 3;

or $R^3$ represents a group expressed by the formula:

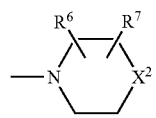

wherein each of $R^6$ and $R^7$ is, independently, a hydrogen atom or an alkyl group having 1 to 3 carbon atoms, $X^2$ represents an oxygen atom, a sulfur atom, a carbonyl group, or $X^2$ represents a group expressed by the formula:

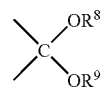

in which each of $R^8$ and $R^9$ is, independently, a hydrogen atom, or an alkyl group having 1 to 3 carbon atoms, or $R^8$ and $R^9$, in combination with each other, represent —$(CH_2)_k$— in which k represents an integer between 1 and 4;

or $X^2$ represents a group expressed by the formula:

in which m represents 0 or 1, $R^{10}$ represents a hydrogen atom, an alkyl group having 1 to 6 carbon atoms, or —$(CH^2)_n X^3$ in which n represents an integer between 1 and 4, and $X^3$ represents an alkoxy group having 1 to 3 carbon atoms, a vinyl group, an ethynyl group, or $X^2$ represents a group expressed by the formula:

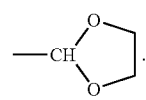

2. The compound of claim 1, wherein said compound is described by formula II.

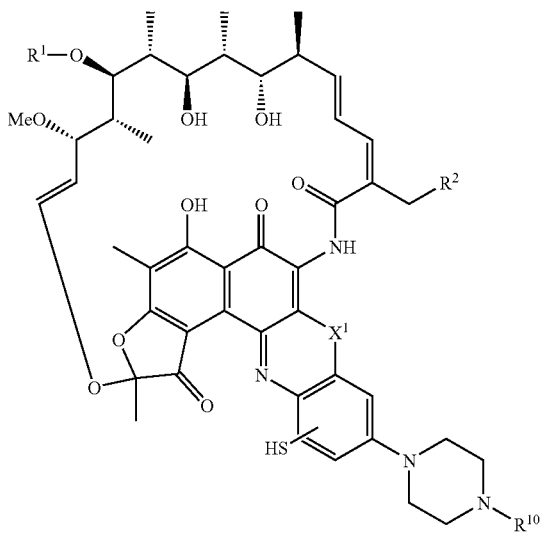

wherein
- $R^1$ is hydrogen or an acetyl group;
- $R^2$ is hydrogen or a hydroxyl group; and $R^{10}$ is selected from the group consisting of methyl, ethyl, iso-propyl, n-propyl, iso-butyl, (S)-sec-butyl, and (R)-sec-butyl.

3. The compound of claim 1, wherein said compound is described by the chemical structure:

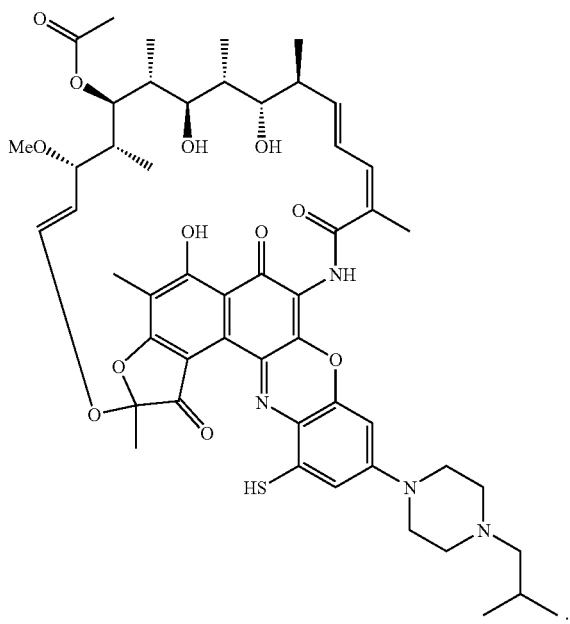

4. The compound of claim 1, wherein said compound is described by the chemical structure:

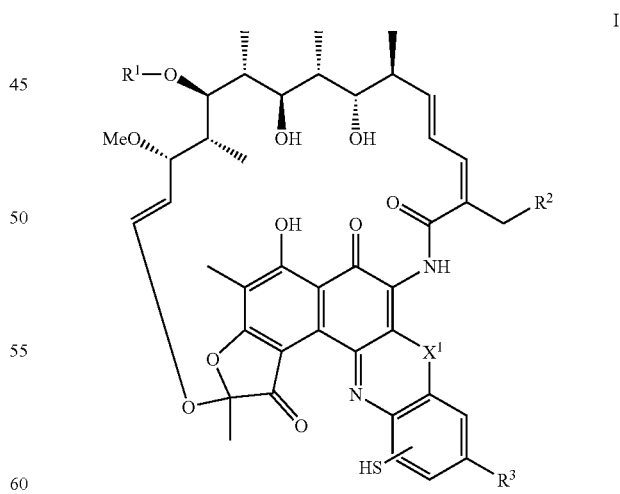

5. The compound of claim 1, wherein said compound is described by the chemical structure:

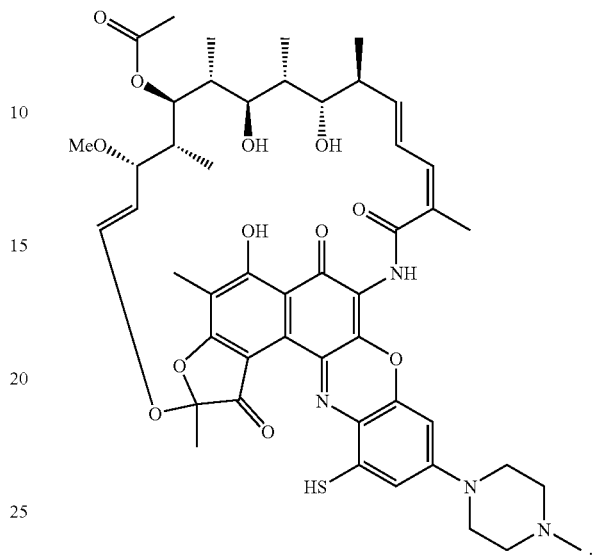

6. A method of treating a Gram-positive bacterial infection, said method comprising contacting the Gram-positive bacteria or a site susceptible to Gram-positive bacterial growth with a compound of claim 1.

7. A pharmaceutical composition comprising a pharmaceutically acceptable carrier or diluent and one or more compounds of formula I:

wherein $X^1$ represents an oxygen atom or a sulfur atom;

$R^1$ represents a hydrogen or an acetyl group;

$R^2$ represents a hydrogen or hydroxyl group; and

R³ represents a hydrogen atom or a group expressed by the formula:

wherein each of R⁴ and R⁵ is, independently, an alkyl group having 1 to 7 carbon atoms, or R⁴ and R⁵ combine to form a 3–8 membered cyclic system, or R³ represents a group expressed by the formula:

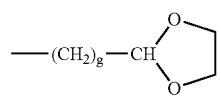

in which g represents an integer between 1 and 3; or R³ represents a group expressed by the formula:

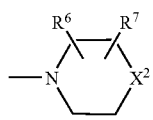

wherein each of R⁶ and R⁷ is, independently, a hydrogen atom or an alkyl group having 1 to 3 carbon atoms, X² represents an oxygen atom, a sulfur atom, a carbonyl group, or X² represents a group expressed by the formula:

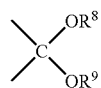

in which each of R⁸ and R⁹ is, independently, a hydrogen atom, or an alkyl group having 1 to 3 carbon atoms, or R⁸ and R⁹, in combination with each other, represent —(CH₂)ₖ— in which k represents an integer between 1 and 4;
or X² represents a group expressed by the formula:

in which m represents 0 or 1, R¹⁰ represents a hydrogen atom, an alkyl group having 1 to 6 carbon atoms, or —(CH²)ₙX³ in which n represents an integer between 1 and 4, and X³ represents an alkoxy group having 1 to 3 carbon atoms, a vinyl group, an ethynyl group, or X² represents a group expressed by the formula:

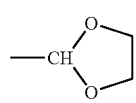

or formula II:

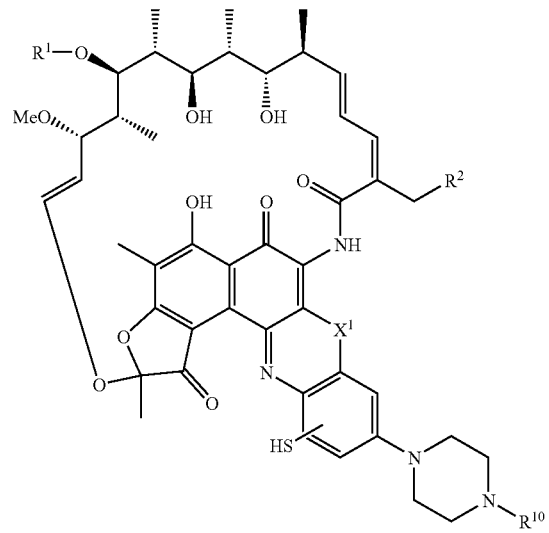

wherein
R¹ is hydrogen or an acetyl group;
R² is hydrogen or a hydroxyl group; and
R¹⁰ is selected from the group consisting of methyl, ethyl, iso-propyl, n-propyl, iso-butyl, (S)-sec-butyl, and (R)-sec-butyl.

8. A method of, treating a Gram-positive bacterial infection in an animal, said method comprising administering to the animal a pharmaceutical composition of claim 7.

9. The method of claim 8, wherein said Gram-positive bacterium is selected from the group consisting of *S. aureus*, methicillin-resistant *S. aureus*, and vancomycin-resistant enterococci.

10. The method of claim 8, said method further comprising co-administering an effective therapeutic amount of an, antibacterial agent.

11. The method of claim 8, wherein said animal is a human.

12. A method of synthesizing a sulfhydryl rifamycin compound of formula VII,

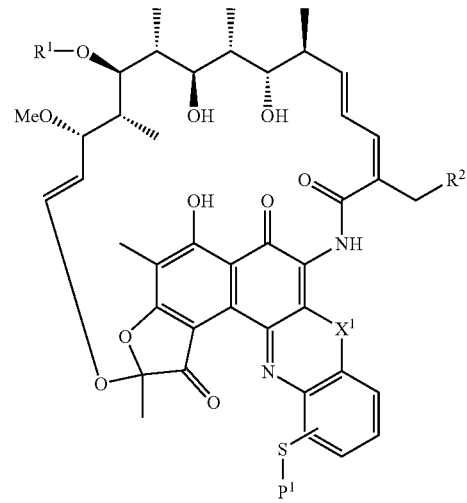

wherein
  $X^1$ represents an oxygen atom or a sulfur atom;
  $R^1$ represents a hydrogen or an acetyl group;
  $R^2$ represents a hydrogen or hydroxyl group; and
  $P^1$ represents a sulfhydryl protecting group,
said method comprising reacting rifamycin S with a compound of formula VIII

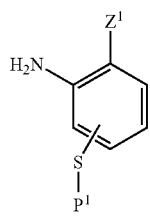

VIII wherein
  $Z^1$ represents a hydroxyl or sulfhydryl group; and
  $P^1$ represents a sulfhydryl protecting group.

13. The method of claim 12, wherein $P^1$ is betacyanoethyl.

14. The method of claim 12, wherein said compound of formula VIII is further described by formula IX

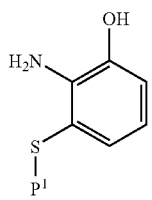

IX wherein $P^1$ is a sulfhydryl protecting group.

15. A method of synthesizing a compound of claim 1, said method comprising the steps of:

(a) reacting rifamycin S with a compound of formula VIII,

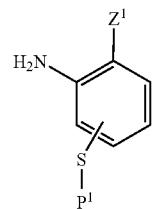

VIII wherein
  $Z^1$ represents a hydroxyl or sulfhydryl group, and
  $P^1$ represents a sulfhydryl protecting group,
to form a sulfhydryl rifamycin compound of formula VII,

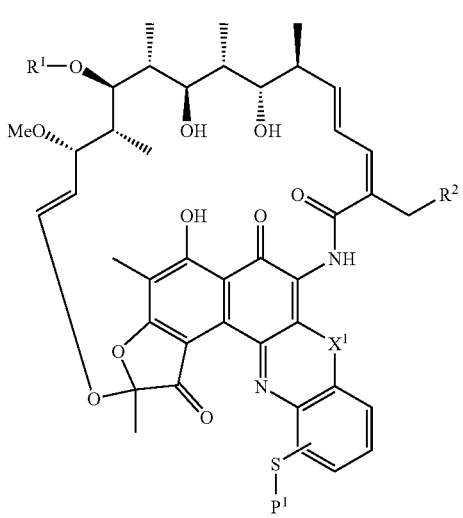

VII wherein
  $X^1$ represents an oxygen atom or a sulfur atom,
  $R^1$ represents a hydrogen or an acetyl group, and
  $R^2$ represents a hydrogen or hydroxyl group, and (b) reacting the sulfhydryl rifamycin compound of step (a) to synthesize a compound of claim 1.

\* \* \* \* \*